(12) United States Patent
Kubota et al.

(10) Patent No.: US 11,409,136 B1
(45) Date of Patent: **\*Aug. 9, 2022**

(54) SUPPORTING PILLARS FOR ENCAPSULATING A FLEXIBLE PCB WITHIN A SOFT HYDROGEL CONTACT LENS

(71) Applicant: ACUCELA INC., Seattle, WA (US)

(72) Inventors: Ryo Kubota, Seattle, WA (US); Gordon Frederick Maccabee, Singapore (SG); Ferry Widjaja, Southampton (GB); Amitava Gupta, Roanoke, VA (US)

(73) Assignee: ACUCELA INC., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/452,549

(22) Filed: Oct. 27, 2021

Related U.S. Application Data

(63) Continuation of application No. 17/301,537, filed on Apr. 6, 2021, now Pat. No. 11,209,672.

(51) Int. Cl.
*G02C 11/00* (2006.01)
*G02C 7/04* (2006.01)
*A61N 5/06* (2006.01)

(52) U.S. Cl.
CPC .............. *G02C 11/10* (2013.01); *G02C 7/04* (2013.01); *A61N 5/0613* (2013.01)

(58) Field of Classification Search
CPC ......... G02C 11/10; G02C 7/04; A61N 5/0613
USPC .................................. 351/41, 159.01, 159.02
See application file for complete search history.

(56) References Cited

U.S. PATENT DOCUMENTS

| | | |
|---|---|---|
| 6,516,808 B2 | 2/2003 | Schulman |
| 7,018,040 B2 | 3/2006 | Blum |
| 8,246,167 B2 | 8/2012 | Legerton |
| 8,432,124 B2 | 4/2013 | Foster |
| 8,662,664 B2 | 3/2014 | Artal Soriano |
| 8,857,983 B2 | 10/2014 | Pugh |
| 9,345,813 B2 | 5/2016 | Hogg |
| 9,763,827 B2 | 9/2017 | Kelleher |
| 9,885,884 B2 | 2/2018 | Drobe |
| 9,918,894 B2 | 3/2018 | Lam |
| RE47,006 E | 8/2018 | To |

(Continued)

FOREIGN PATENT DOCUMENTS

| | | |
|---|---|---|
| EP | 3413116 | 12/2018 |
| KR | 20180038359 | 4/2018 |

(Continued)

OTHER PUBLICATIONS

Adler, Daniel, et al., "The possible effect of under correction on myopic progression in children," Clin Exp Optom., 89:315-321 (2006).

(Continued)

*Primary Examiner* — Tuyen Tra
(74) *Attorney, Agent, or Firm* — FisherBroyles LLP; John Shimmick

(57) ABSTRACT

A contact lens may include a body of contact lens material extending between a first surface and a second surface. An electromechanical component may be supported in the contact lens material between the first surface and the second surface. A support comprising a plurality of pillars may be formed of the contact lens material and may extend from at least one of the first surface and the second surface to the electromechanical component.

19 Claims, 15 Drawing Sheets

(56) References Cited

U.S. PATENT DOCUMENTS

| | | | |
|---|---|---|---|
| 10,133,092 | B2 | 11/2018 | Tsubota |
| 10,146,067 | B2 | 12/2018 | Tsai |
| 10,231,897 | B2 | 3/2019 | Tse |
| 10,268,050 | B2 | 4/2019 | To |
| 10,288,909 | B1 | 5/2019 | Youssef |
| 10,788,686 | B2 | 9/2020 | Tsai |
| 10,884,264 | B2 | 1/2021 | Hones |
| 10,921,612 | B2 | 2/2021 | Zhou |
| 10,993,515 | B1 | 5/2021 | Kim |
| 11,000,186 | B2 | 5/2021 | Linder |
| 11,163,166 | B1 | 11/2021 | Ebert |
| 11,187,921 | B2 | 11/2021 | Zhou |
| 2002/0186345 | A1 | 12/2002 | Duppstadt |
| 2003/0011745 | A1 | 1/2003 | Molebny |
| 2004/0237971 | A1 | 12/2004 | Radhakrishnan |
| 2004/0246441 | A1 | 12/2004 | Stark |
| 2004/0257529 | A1 | 12/2004 | Thomas |
| 2006/0082729 | A1 | 4/2006 | To |
| 2007/0002452 | A1 | 1/2007 | Munro |
| 2007/0076217 | A1 | 4/2007 | Baker |
| 2007/0115431 | A1 | 5/2007 | Smith, III |
| 2007/0127349 | A1 | 6/2007 | Hotta |
| 2008/0291391 | A1 | 11/2008 | Meyers |
| 2008/0309882 | A1 | 12/2008 | Thorn |
| 2009/0002631 | A1 | 1/2009 | Campbell |
| 2009/0187242 | A1 | 7/2009 | Weeber |
| 2009/0204207 | A1 | 8/2009 | Blum |
| 2010/0076417 | A1 | 3/2010 | Suckewer |
| 2010/0296058 | A1 | 11/2010 | Ho |
| 2011/0085129 | A1 | 4/2011 | Legerton |
| 2011/0153012 | A1 | 6/2011 | Legerton |
| 2011/0157554 | A1 | 6/2011 | Kawai |
| 2011/0202114 | A1 | 8/2011 | Kessel |
| 2012/0199995 | A1 | 8/2012 | Pugh |
| 2012/0206485 | A1 | 8/2012 | Osterhout |
| 2012/0212399 | A1 | 8/2012 | Border |
| 2012/0215291 | A1 | 8/2012 | Pugh |
| 2013/0027655 | A1 | 1/2013 | Blum |
| 2013/0278887 | A1 | 10/2013 | Legerton |
| 2014/0039048 | A1 | 2/2014 | Olof |
| 2014/0039361 | A1 | 2/2014 | Siu |
| 2014/0194773 | A1 | 7/2014 | Pletcher |
| 2014/0218647 | A1 | 8/2014 | Blum |
| 2014/0240665 | A1 | 8/2014 | Pugh |
| 2014/0268029 | A1 | 9/2014 | Pugh |
| 2014/0277291 | A1 | 9/2014 | Pugh |
| 2015/0057701 | A1 | 2/2015 | Kelleher |
| 2015/0109574 | A1 | 4/2015 | Tse |
| 2015/0160477 | A1 | 6/2015 | Dai |
| 2015/0241706 | A1 | 8/2015 | Schowengerdt |
| 2016/0056498 | A1 | 2/2016 | Flitsch |
| 2016/0067037 | A1 | 3/2016 | Rosen |
| 2016/0091737 | A1 | 3/2016 | Kim |
| 2016/0143801 | A1 | 5/2016 | Lam |
| 2016/0158486 | A1 | 6/2016 | Colbaugh |
| 2016/0212404 | A1 | 7/2016 | Maiello |
| 2016/0270656 | A1 | 9/2016 | Samec |
| 2016/0377884 | A1 | 12/2016 | Lau |
| 2017/0000326 | A1 | 1/2017 | Samec |
| 2017/0001032 | A1 | 1/2017 | Samec |
| 2017/0010480 | A1 | 1/2017 | Blum |
| 2017/0014074 | A1 | 1/2017 | Etzkorn |
| 2017/0055823 | A1 | 3/2017 | Lu |
| 2017/0072218 | A1 | 3/2017 | Rucker |
| 2017/0097519 | A1 | 4/2017 | Lee |
| 2017/0184875 | A1 | 6/2017 | Newman |
| 2017/0229730 | A1 | 8/2017 | Flitsch |
| 2017/0236255 | A1 | 8/2017 | Wetzstein |
| 2017/0270636 | A1 | 9/2017 | Shtukater |
| 2017/0276963 | A1 | 9/2017 | Brennan |
| 2017/0307779 | A1 | 10/2017 | Marullo |
| 2018/0017810 | A1 | 1/2018 | Wu |
| 2018/0017814 | A1 | 1/2018 | Tuan |
| 2018/0052319 | A1 | 2/2018 | McCabe |
| 2018/0055351 | A1 | 3/2018 | Yates |
| 2018/0074322 | A1 | 3/2018 | Rousseau |
| 2018/0090958 | A1 | 3/2018 | Steger |
| 2018/0092738 | A1 | 4/2018 | Tai |
| 2018/0136486 | A1 | 5/2018 | Macnamara |
| 2018/0161231 | A1 | 6/2018 | Tse |
| 2018/0173010 | A1 | 6/2018 | Harant |
| 2018/0188556 | A1 | 7/2018 | Portney |
| 2018/0221140 | A1 | 8/2018 | Rosen |
| 2018/0275427 | A1 | 9/2018 | Lau |
| 2018/0345034 | A1 | 12/2018 | Butzloff |
| 2019/0033618 | A1 | 1/2019 | Choi |
| 2019/0033619 | A1 | 1/2019 | Neitz |
| 2019/0038123 | A1 | 2/2019 | Linder |
| 2019/0049730 | A1 | 2/2019 | Miller |
| 2019/0076241 | A1 | 3/2019 | Alarcon Heredia |
| 2019/0107734 | A1 | 4/2019 | Lee |
| 2019/0113757 | A1 | 4/2019 | Van Heugten |
| 2019/0129204 | A1 | 5/2019 | Tsubota |
| 2019/0227342 | A1 | 7/2019 | Brennan |
| 2019/0235279 | A1 | 8/2019 | Hones |
| 2019/0247675 | A1 | 8/2019 | Legerton |
| 2019/0250432 | A1 | 8/2019 | Kim |
| 2019/0314147 | A1 | 10/2019 | Blum |
| 2020/0033637 | A1 | 1/2020 | Jamshidi |
| 2020/0089023 | A1 | 3/2020 | Zhou |
| 2020/0110265 | A1 | 4/2020 | Serdarevic |
| 2020/0133024 | A1 | 4/2020 | Paune Fabre |
| 2020/0142219 | A1 | 5/2020 | Rousseau |
| 2020/0183169 | A1 | 6/2020 | Peng |
| 2020/0360184 | A1 | 11/2020 | Xiao |
| 2021/0018762 | A1 | 1/2021 | Zheleznyak |
| 2021/0031051 | A1 | 2/2021 | Kubota |
| 2021/0048690 | A1 | 2/2021 | Guillot |
| 2021/0069524 | A1 | 3/2021 | Kubota |
| 2021/0263336 | A1 | 8/2021 | Gupta |
| 2021/0298440 | A1 | 9/2021 | Kim |
| 2021/0356767 | A1 | 11/2021 | Kubota |
| 2021/0379399 | A1 | 12/2021 | Buscemi |
| 2021/0382325 | A1 | 12/2021 | Kubota |
| 2021/0382326 | A1 | 12/2021 | Kubota |
| 2021/0389607 | A1 | 12/2021 | Buscemi |

FOREIGN PATENT DOCUMENTS

| | | |
|---|---|---|
| KR | 20180038359 A | 4/2018 |
| WO | 2009074638 | 6/2009 |
| WO | 2009074638 A3 | 6/2009 |
| WO | 2009121810 | 10/2009 |
| WO | 2010043599 | 4/2010 |
| WO | 2011089042 | 7/2011 |
| WO | 2012136470 | 10/2012 |
| WO | 2013087518 | 6/2013 |
| WO | 2014033035 | 3/2014 |
| WO | 2014191460 | 12/2014 |
| WO | 2015063097 | 5/2015 |
| WO | 2015186723 | 12/2015 |
| WO | 2015192117 | 12/2015 |
| WO | 2018014712 | 1/2018 |
| WO | 2018014960 | 1/2018 |
| WO | 2018085576 | 5/2018 |
| WO | 2018208724 | 11/2018 |
| WO | 2019114463 | 6/2019 |
| WO | 2019191510 | 10/2019 |
| WO | 2019217241 | 11/2019 |
| WO | 2020014074 | 1/2020 |
| WO | 2020014613 | 1/2020 |
| WO | 2020028177 | 2/2020 |
| WO | 2020069232 | 4/2020 |
| WO | 2021022193 | 2/2021 |
| WO | 2021056018 | 3/2021 |
| WO | 2021168481 | 8/2021 |
| WO | 2021231684 | 11/2021 |
| WO | 2021252318 | 12/2021 |

(56) References Cited

FOREIGN PATENT DOCUMENTS

| WO | 2021252319 | 12/2021 |
|---|---|---|
| WO | 2021252320 | 12/2021 |

OTHER PUBLICATIONS

Aleman, Andrea C., et al.,, "Reading and Myopia: Contrast Polarity Matters," Scientific Reports, 8 pages (2018).

Arden, G.B., et al., "Does dark adaptation exacerbate diabetic retinopathy? Evidence and a linking hypothesis," Vision Research 38:1723-1729 (1998).

Arden, GB, et al., "Regression of early diabetic macular edema is associated with prevention of dark adaptation", in Eye, (2011). 25, pp. 1546-1554.

Benavente-Perez, A., et al., "Axial Eye Growth and Refractive Error Development Can be Modified by Exposing the Peripheral Retina to Relative Myopic or Hyperopic Defocus," Invest Ophthalmol Vis Sci., 55:6765-6773 (2014).

Bonar, JR, et al., "High brightness low power consumption microLED arrays", in SPIE DigitalLibrary.org/conference-proceedings-of-spie, SPIE OPTO, 2016, San Francisco, California, United States, Abstract Only.

Carr, Brittany J., et al., "The Science Behind Myopia," retrieved from https://webvision.med.utah.edu/book/part-xvii-refractive-errors/the-science-behind-myopia-by-brittany-j-carr-and-william-k-stell/, 89 pages (2018).

Chakraborty, R., et al., "Diurnal Variations in Axial Length, Choroidal Thickness, Intraocular Pressure, and Ocular Biometrics," IOVS, 52(8):5121-5129 (2011).

Chakraborty, R., et al., "Hyperopic Defocus and Diurnal Changes in Human Choroid and Axial Length," Optometry and Visual Science, 90(11):1187-1198 (2013).

Chakraborty, R., et al., "Monocular Myopic Defocus and Daily Changes in Axial Length and Choroidal Thickness of human Eyes," Exp Eye Res, 103:47-54 (2012).

Cooper, J., et al., "Current status of the development and treatment of myopia", Optometry, 83:179-199 (2012).

Cooper, J., et al., "A Review of Current Concepts of the Etiology and Treatment of Myopia," Eye & Contact Lens, 44(4):231-247 (Jul. 2018).

Demory, B., et al., "Integrated parabolic microlenses on micro LED color pixels", in Nanotechnology, (2018); 29, 16, pp. 1018, Abstract Only.

Dolgin, Elie, "The Myopia Boom," Nature 519:276-278 (2015).

Edrington, Timothy B., "A literature review: The impact of rotational stabilization methods on toric soft contact lens performance," Contact Lens & Anterior Eye, 34:104-110 (2011).

Flitcroft, D.I., "The complex interactions of retinal, optical and environmental factors in myopia aetiology," 31(6):622-660 (2012).

Garner, L.F., et al., "Crystalline Lens Power in Myopia," Optometry and Vision Science, 69:863-865 (1992).

Gwiazda, Jane, "Treatment Options for Myopia," retrieved from https://www.ncbi.nlm.nih.gov/pmc/articles/PMC2729053/, Optom Vis Sci., 86(6):624-628 (Jun. 2009).

Gwiazda, Jane, et al., "A Randomized Clinical Trial of Progressive Addition Lenses versus Single Vision Lenses on the Progression of Myopia in Children", Invest Ophthalmol Vis Sci, 44:1492-500 [PubMed: 12657584] (2003).

Haglund, Erik, et al., "Multi-wavelength VCSEL arrays using high-contrast gratings," Proc. of SPIE vol. 10113, 7 pages (2017).

Hammond, D.S., et al., "Dynamics of active emmetropisation in young chicks—influence of sign and magnitude of imposed defocus" Ophthalmic Physiol Opt. 33:215-222 (2013).

Henry W., "MicroLED Sources enable diverse ultra-low power applications", in Photonic Spectra, 2013.

International Application No. PCT/US2021/036100, filedJune 7, 2021 (86 pages).

International Patent Application No. PCT/US2021/032162, filed May 13, 2021 (58 pages).

International Patent Application No. PCT/US2021/036102, filed Jun. 7, 2021 (67 pages).

International Patent Application No. PCT/US2021/070166, filed Feb. 19, 2021 (79 pages).

Jayaraman, V., et al., "Recent Advances in MEMS-VCSELs for High Performance Structural and Functional SS-OCT Imaging," Proc. of SPIE vol. 8934, retrieved from http://proceedings.spiedigitallibrary.org/ on Dec. 1, 2015 (2014).

Jones, D., "Measure Axial Length to Guide Myopia Management," Review of Myopia Management, 5 pages (Apr. 9, 2020).

Kur, Joanna, et al., "Light adaptation does not prevent early retinal abnormalities in diabetic rats," Scientific Reports, 8 pages (Feb. 8, 2016).

Lagreze, Wolf A., et al., "Preventing Myopia," retrieved from https://www.ncbi.nlm.nih.gov/pmc/articles/PMC5615392/, Dtsch Arztebl Int., 114(35-36):575-580 (Sep. 2017).

Lam, Carly Siu Yin, et al., "Defocus Incorporated Multiple Segments (DIMS) spectacle lenses slow myopia progression: a 2-year randomised clinical trial," Br. J. Ophthalmol. 0:1-6 (2019).

Leo, Seo-Wei, et al., "An evidence-based update on myopia and interventions to retard its progression," J AAPOS, 15(2):181-189 (Apr. 2011).

Lingley, A.R., et al, : A single pixel wireless contact lens display, in J Micromech. Microeng., 2011; 21, 125014; doi:10.1088/0960-1317/21/12/125014, Abstract Only.

Martin, J.A., et al., "Predicting and Assessing Visual Performance with Multizone Bifocal Contact Lenses," Optom Vis Sci, 80(12):812-819 (2003).

Matkovic, K., et al., "Global Contrast Factor—a New Approach to Image Contrast," Computational Aesthetics in Graphics, Visualization and Imaging, 9 pages (2005).

McKeague C, et al. "Low-level night-time light therapy for age-related macular degeneration (ALight): study protocol for a randomized controlled trial", in Trials 2014, 15:246, http://www.trialsjournal.com/content/15/1/246.

Moreno, I, "Creating a desired lighting pattern with an LED array" in Aug. 2008, Proceedings of SPIE—The International Society for Optical Engineering 7058, DOI: 10.1117/12.795673.

Moreno, I., "Modeling the radiation pattern of LEDS", in Optics Express, 2008; 16, 3 pp. 1808.

Nickla, Debora L., et al., "Brief hyperopic defocus or form deprivation have varying effects on eye growth and ocular rhythms depending on the time-of-day of exposure," Exp Eye Res. 161:132-142 (Aug. 2017).

Ramsey, DJ, and Arden, GB, "Hypoxia and dark adaptation in diabetic retinopathy: Interactions, consequences and therapy", in Microvascular Complications-Retinopathy (JK Sun, ed.), Cur Dab Rep (2015) 15: 118, DOI 10.1007/s11892-015-0686-2, Abstract Only.

Read, Scott A., et al., "Choroidal changes in human myopia: insights from optical coherence tomography imaging," Clin Exp Optom, 16 pages (2018).

Read, Scott A., et al., "Human Optical Axial Length and Defocus," IOVS, 51(12):6262-6269 (2010).

Shivaprasad, S, et al., "Clinical efficacy and safety of a light mask for prevention of dark adaptation in treating and preventing progression of early diabetic macular oedema at 24 months (CLEOPATRA): a multicentre, phase 3, randomised controlled trial," in www.thelancet.com/diabetes-endocrinology vol. 6, pp. 382-391 ( May 2018).

Smith, III, Earl L., "Optical treatment strategies to slow myopia progression: Effects of the visual extent of the optical treatment zone," retrieved from https://www.ncbi.nlm.nih.gov/pmc/articles/PMC3624048/, Exp Eye Res., 114:77-88 (Sep. 2013).

Srinivasan, S., "Ocular axes and angles: Time for better understanding," J. Cataract Refract. Surg., 42:351-352 (Mar. 2016).

Torii, Hidemasa, et al., "Violet Light Exposure Can Be a Preventive Strategy Against Myopia Progression," EBioMedicine 15:210-219 (2017).

U.S. Appl. No. 17/304,666, filed Jun. 24, 2021 (67 pages).
U.S. Appl. No. 17/302,479, filed May 4, 2021 (60 pages).
U.S. Appl. No. 17/302,827, filed May 13, 2021 (52 pages).
U.S. Appl. No. 17/303,889, filed Jun. 9, 2021 (69 pages).

(56) References Cited

OTHER PUBLICATIONS

U.S. Appl. No. 17/304,630, filed Jun. 23, 2021 (68 pages).
U.S. Appl. No. 17/304,691, filed Jun. 24, 2021 (88 pages).
Wallman, Josh, et al., "Homeostasis of Eye Growth and the Question of Myopia," Neuron, 43:447-468 (2004).
Wolffsohn, James A., et al., "Impact of Soft Contact Lens Edge Design and Midperipheral Lens Shape on the Epithelium and Its Indentation With Lens Mobility," IOVS, 54(9):6190-6196 (2013).

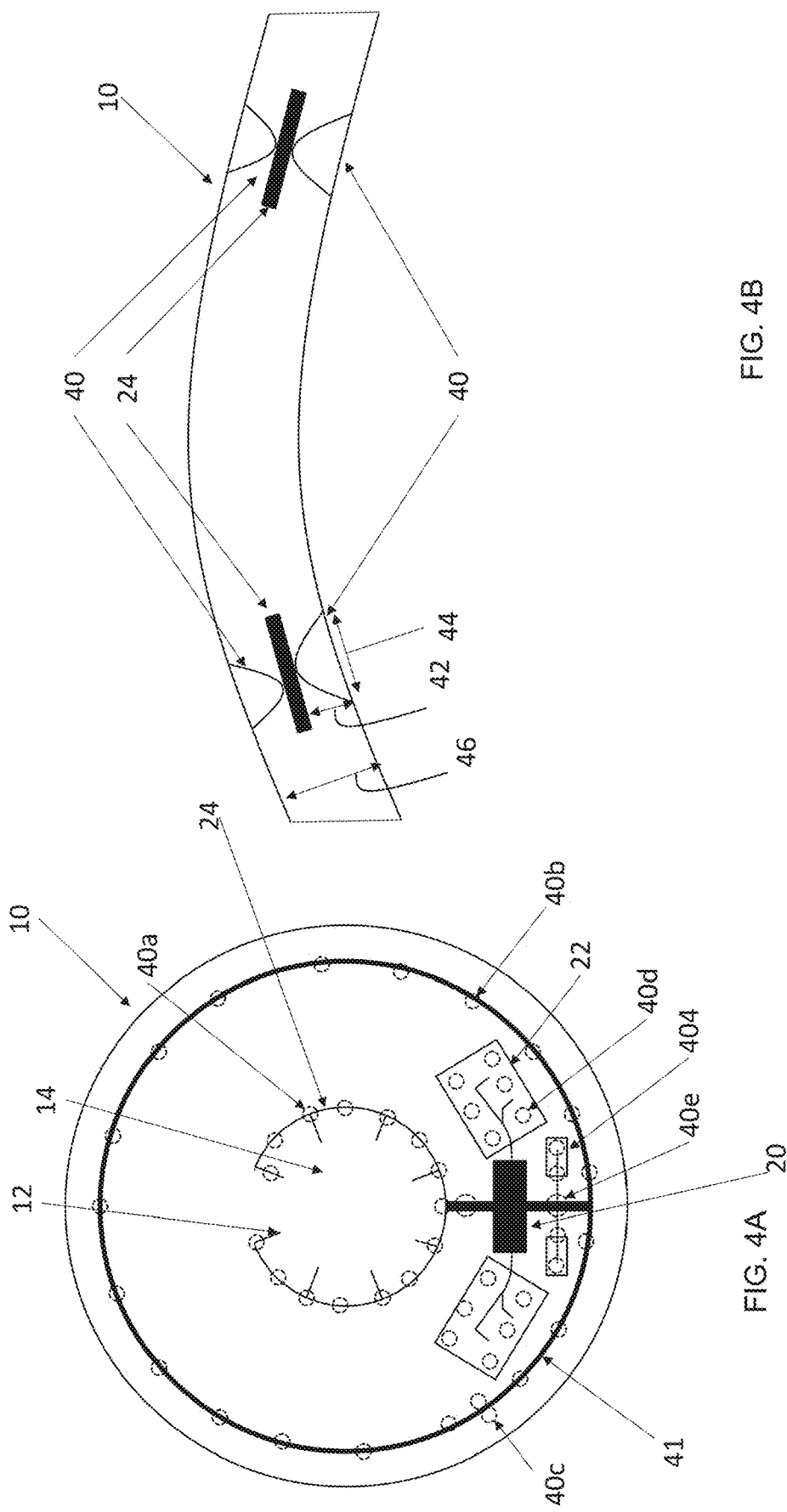

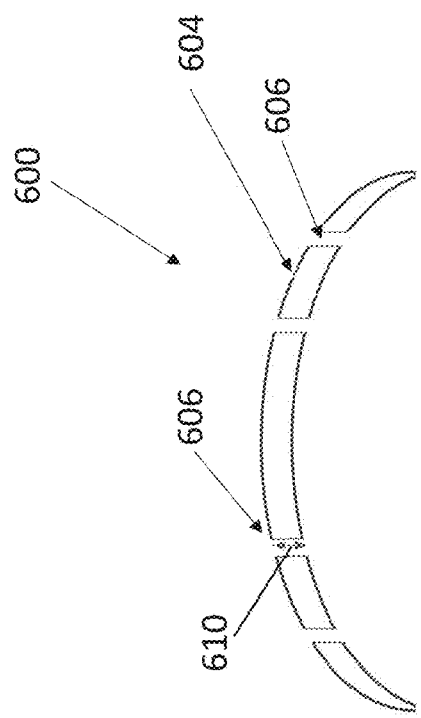
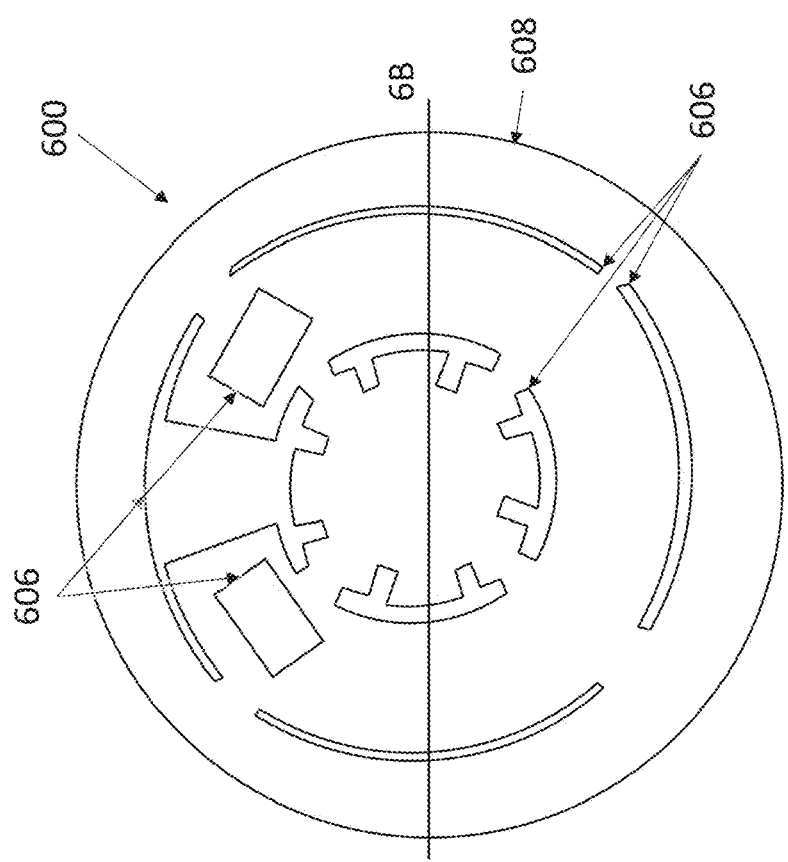
FIG. 6B
FIG. 6A

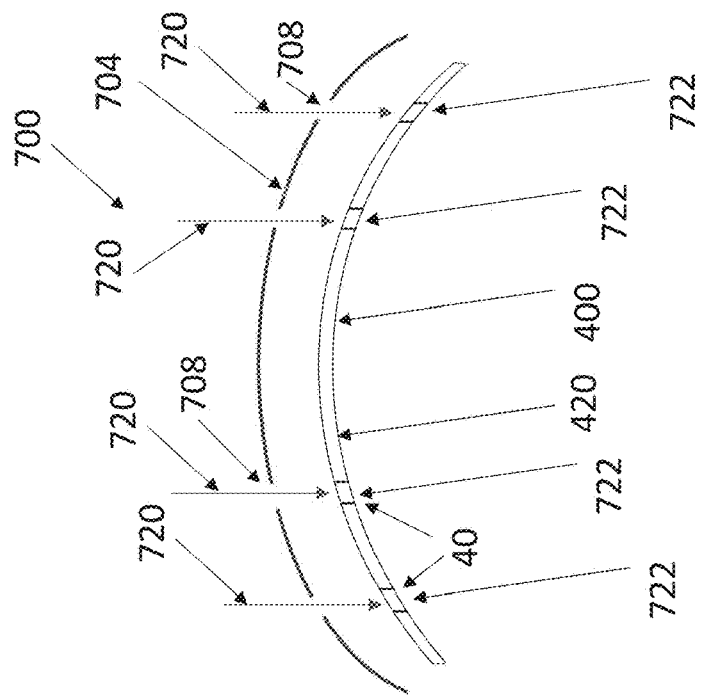
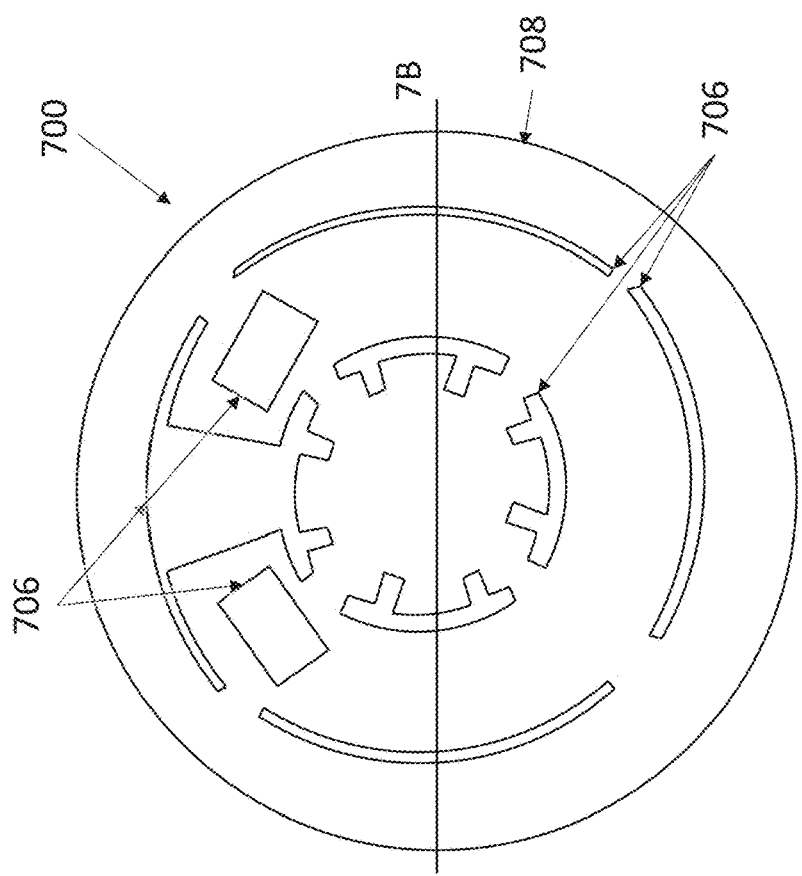
FIG. 7B
FIG. 7A

SUPPORTING PILLARS FOR ENCAPSULATING A FLEXIBLE PCB WITHIN A SOFT HYDROGEL CONTACT LENS

RELATED APPLICATIONS

This application is a continuation of U.S. patent application Ser. No. 17/301,537, filed Apr. 6, 2021, now U.S. Pat. No. 11,209,672, issued Dec. 28, 2021, the disclosure of which is incorporated, in its entirety, by this reference.

BACKGROUND

Electronic contact lenses, sometimes referred to as eCLs, are contact lenses that include electrical, mechanical, or other components. Prior electronic contact lenses are less than ideal for a number of reasons. The electronic contact lenses can be difficult to manufacture in a way that results in a contact lens that is safe and comfortable for the patient to wear and the resulting lenses have low durability. A potential problem that can arise is that the soft contact lens material can separate from the electronics.

SUMMARY

The electronic contact lenses disclosed herein, and the disclosed fabrication processes used to manufacture contact lenses, provide for an electronic contact lens comprising components that are encapsulated within contact lens material and supported by one or more supports. The components can be configured in many ways and may comprise one or more of display components, or active components to provide therapy such as light therapy. In some embodiments, the supports used in the manufacturing process aid in aligning the components between the surfaces of the contact lens and in encapsulating the electronic components within the body of the contact lens. The supports can be sized and shaped in many ways and may comprise pillars to support the electronical components during fabrication. Encapsulating the components within the body of the contact lens allows for a safer and more comfortable experience for the patient, and also improves durability of the contact lenses.

The fabrication of the contact lens is also improved. Supports formed from contact lens material are formed on a mold prior to placing the components in the mold and forming the rest of the contact lens body. The supports aid in accurately positioning the contact lens components in the contact lens mold and with respect to the final shape of the contact lens. The supports also hold the contact lens components in a suspended location within the uncured contact lens material during fabrication. This allows for better encapsulation of the components withing the final contact lens body.

A contact lens may include a body of contact lens material extending between a first surface and a second surface. An electromechanical component may be suspended in the contact lens material between the first surface and the second surface. A support may be formed of the contact lens material and may extend from at least one of the first surface and the second surface to the electromechanical component.

A method of fabricating a contact lens may include forming a support of contact lens material on a first contact lens mold. The support of contact lens material may be partially cured. Electromechanical components may be placed on the support. The mold may be filled with contact lens material. The contact lens material may be cured.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 4A shows a contact lens with supports for supporting the electrical and mechanical components in the contact lens, in accordance with some embodiments;

FIG. 4B shows a cross section of the contact lens with supports of FIG. 4A, in accordance with some embodiments;

FIGS. 6A and 6B show a support mask, in accordance with some embodiments;

FIGS. 7A and 7B show a support mask, in accordance with some embodiments;

DETAILED DESCRIPTION

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The presently disclosed methods and apparatus can be configured in many ways to provide contact lenses for retinal stimulation, as described herein.

The presently disclosed methods and apparatus are well suited for combination with many prior devices such as, one or more of an ophthalmic device, a contact lens, an implantable device, a corneal onlay, a corneal inlay, a corneal prosthesis, an intraocular lens, a spectacle lens, a virtual reality (VR) display or an augmented reality (AR) display. Although specific reference is made to contact lenses, the presently disclosed methods and apparatus are well suited for use with any of the aforementioned devices, and a person of ordinary skill in the art will readily appreciate how one or more of the presently disclosed components can be interchanged among devices, based on the teachings provided herein.

The presently disclosed methods and apparatus are well suited for use with lenses for light therapy to treat refractive error of the eye to treat myopia. Work in relation to the present disclosure suggests that changes to choroidal thickness in response to stimulation on regions of the eye can be localized to regions near the stimulated regions, which can provide a somewhat localized response in accordance with some embodiments. In some embodiments, the changes to one or more of the choroid or sclera comprise a differential change, in which the changes to the one or more of the choroid or sclera are greater near the regions of stimulation than at corresponding regions remote from the stimulation (e.g. corresponding locations at an axis 90 degrees from the region of stimulation).

Work in relation to the present disclosure suggests systems and methods for fabricating such lenses may include fabricating supporting pillars for supporting electrical and mechanical systems, such as embedded electronics and optics, during and after fabrication.

Figure 1:
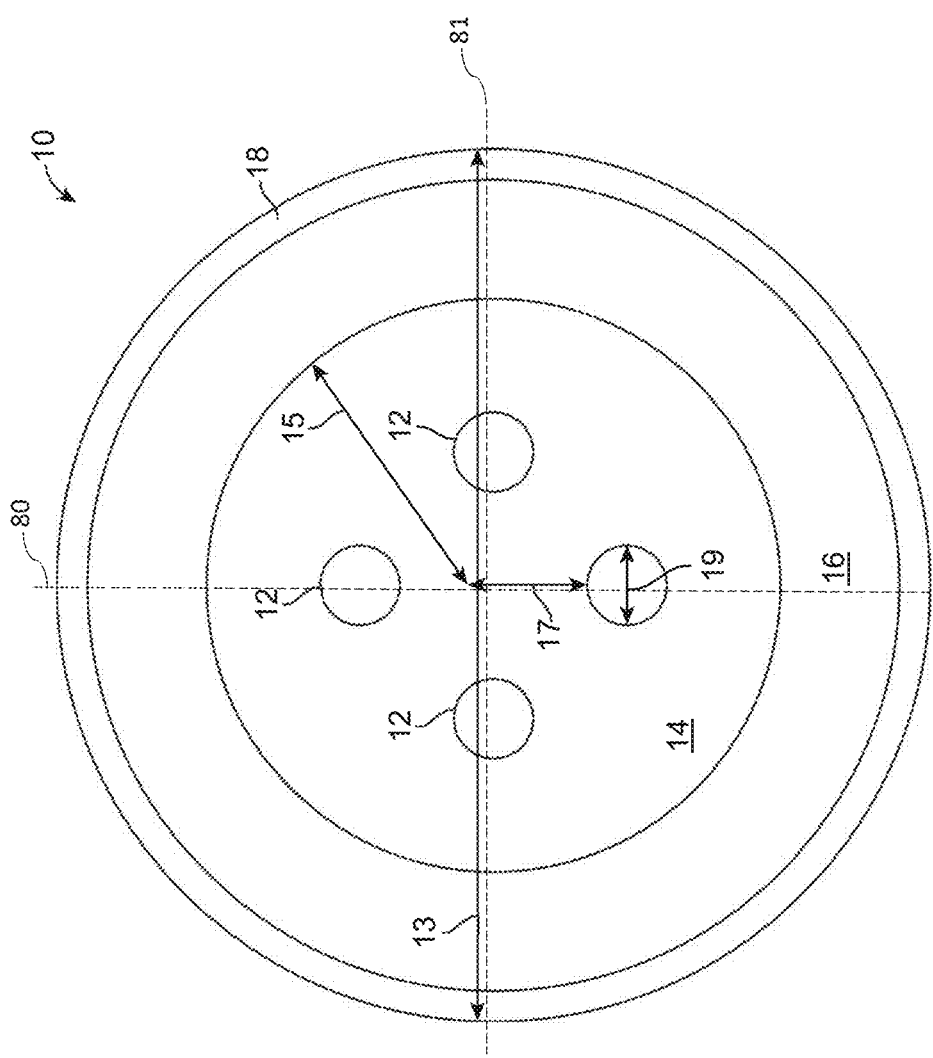
FIG. 1 shows a contact lens, in accordance with some embodiments.
Figure 2:
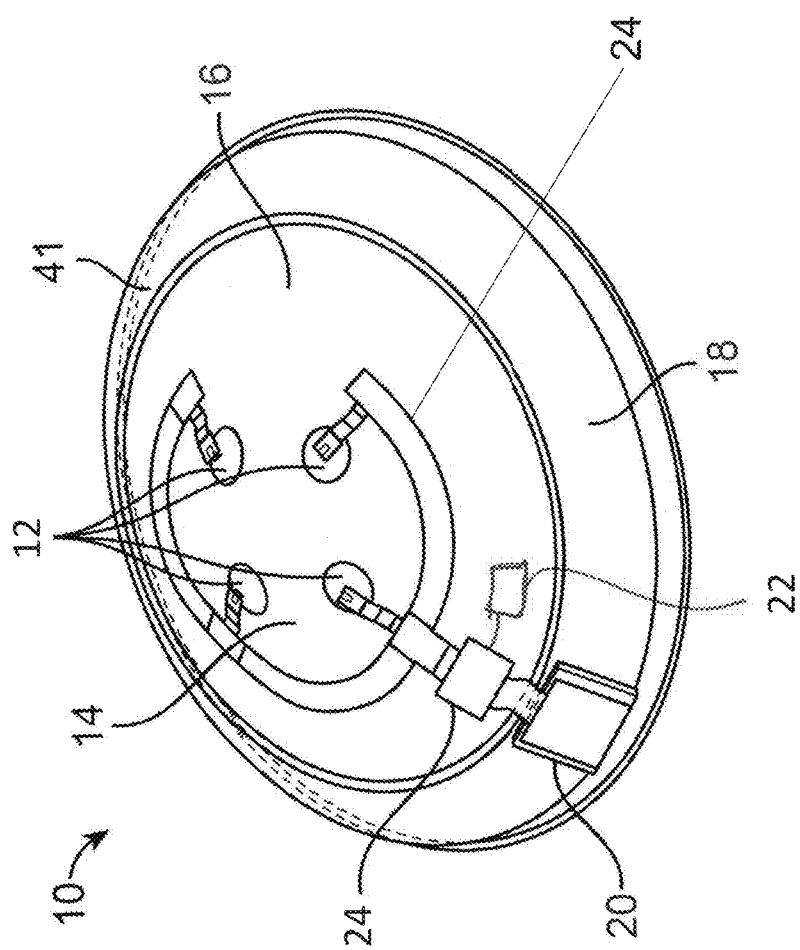
FIG. 2 shows a contact lens, in accordance with some embodiments.

FIGS. 1 and 2 depict a lens such as a contact lens 10 configured to project a defocused image on the retina away from the central field that includes the macula in order to stimulate a change in choroidal thickness. Although reference is made to a contact lens, the lens 10 may comprise a lens of one or more of a contact lens, a corneal onlay, a corneal inlay, a corneal prosthesis, or an intraocular lens.

In some embodiments, for the treatment of astigmatism, the contact lens 10 comprises a first astigmatic axis 80 and a second astigmatic axis 81. The plurality of light sources, such as projection units 12, is arranged with respect to the astigmatic axes to provide different amounts of stimulation to different regions of the peripheral retina. In some embodiments, the light sources such as projection units 12 are located along the astigmatic axis, although the light sources may be located at other locations. The light sources can be configured to provide different amounts of stimulation to the peripheral retina in accordance with the refractive error of the eye. In some embodiments, the light sources are configured to provide different amounts of illumination along different axes in order to promote different changes in choroidal and scleral tissue corresponding to different changes in axial length as described herein. The contact lens may comprise a rotationally stabilized contact lens, and the light sources can be located on the contact lens so as to correspond to the astigmatic axes of the eye when the lens is stabilized on the eye, for example. The contact lens may comprise an optical zone configured to correct astigmatic refractive errors in accordance with the first axis 80 and the second axis 81.

In some embodiments, for the treatment of spherical refractive errors of the eye, the plurality of light sources, such as projection units 12, are arranged with symmetrically with respect to central axis of the contact lens, the center of the contact lens, or another location of the contact lens. The symmetry may be rotational symmetry, such that the light sources are arranged on a circumference centered on the location of the contact lens.

This contact lens 10 comprises a base or carrier contact lens comprising embedded electronics and optics. The base soft contact lens 10 is made of a biocompatible material such as a hydrogel or a silicone hydrogel polymer designed to be comfortable for sustained wear. The contact lens comprises a maximum overall distance across, e.g. a diameter 13. The biocompatible material can encapsulate the components of the soft contact lens 10. For example, the components may be embedded within the biocompatible material. In some embodiments, the contact lens 10 has a central optical zone 14 designed to cover the pupil of a wearer under many illumination conditions. In some embodiments, the optical zone comprises a circular zone defined with a radius 15. In some embodiments, a plurality of projection units 12 are located a distance 17 from a center of the optical zone. Each of the plurality of projection units 12 comprises a distance across 19. In some embodiments, the distances between the projection units are sized to place the projection units outside the optical zone to stimulate a peripheral region of the retina, although the projection units can also be placed inside the optical zone to stimulate the peripheral retina as described herein.

The optical zone 14 can be appropriately sized for the pupil of the eye and the illumination conditions during treatment. In some embodiments, the optical zone comprises a diameter of 6 mm, for example when the contact lens is configured for use during the day. The optical zone 14 may have a of diameter within a range from 6 mm to 9 mm, for example within a range from 7.0 mm to 8.0 mm. The central optical zone 14 is designed to provide emmetropic correction or other suitable correction to the wearer and may be provided with both spherical and astigmatic correction. The central optical zone 14 is circumscribed by an outer annular zone, such as a peripheral zone 16 of width in a range 2.5 mm to 3.0 mm. The peripheral zone 16, sometimes referred to as the blend zone is primarily designed to provide a good fit to the cornea, including good centration and minimum decentration. The outer annular zone is surrounded by an outermost edge zone 18 of width in the range from 0.5 mm to 1.0 mm. The optical zone 14 is configured to provide refractive correction and can be spherical, toric or multifocal in design, for example with a visual acuity of 20/20 or better. The outer annular zone peripheral to the optical zone 14 is configured to fit the corneal curvature and may comprise rotational stabilization zones for translational and rotational stability, while allowing movement of the contact lens 10 on the eye following blinks. The edge zone 18 may comprise a thickness within a range from 0.05 mm to 0.15 mm and may end in a wedge shape. The overall diameter 13 of the soft contact lens 10 can be within a range from 12.5 mm to 15.0 mm, for example within a range from 13.5 mm to 14.8 mm.

The contact lens 10 includes a plurality of embedded projection units 12. Each of the plurality of projection units 12 comprises a light source and one or more optics to focus light in front of the retina as described herein. Each of the optics may comprise one or more of a mirror, a plurality of mirrors, a lens, a plurality of lenses, a diffractive optic, a Fresnel lens, a light pipe or a wave guide. The contact lens 10 may comprise a battery 20 and a sensor 22. The contact lens 10 may comprise a flex printed circuit board (PCB) 24, and a processor can be mounted on the flex PCB 24. The processor can be mounted on the PCB 24 and coupled to the sensor 22 and the plurality of light sources 30. The soft contact lens 10 may also comprise wireless communication circuitry and one or more antennae 41 for electronic communication and for inductively charging the battery 20 of the contact lens 10. Although reference is made to a battery 20, the contact lens 10 may comprise any suitable energy storage device.

The projection units 12 can be configured to provide defocused images to the peripheral portion of the retina as described herein and may include light sources and projection optics. In some embodiments, one or more projection optics are configured with the light sources to project a defocused image from the light sources onto the peripheral retina away from the central visual field that includes the macula in order to stimulate a change in choroidal thickness, such as an increase or decrease in cordial thickness. The one or more projection units 12 can be configured to stimulate the retina without degrading central vision and corresponding images formed on one or more of the foveal or macular regions of the retina. In some embodiments, the one or more projection optics do not decrease the image forming characteristics of the vision correction optics prescribed to correct refractive errors of the wearers. This configuration can allow the wearer to have good visual acuity while receiving therapy from the defocused images as described herein.

In some embodiments, the light from light sources of the projection units 12 are columnated and focused by one or more projection optics, as described herein. The function of the light sources and the projection optics is to substantially collimate the light emitted by the light sources and focus it at a focus that is designed to be in the front of or behind the retina to provide appropriate defocus to stimulate a change in choroidal thickness. For myopic defocus, the focused images may appear approximately 1.5 mm to 2.5 mm in front of the peripheral retina and myopic by about 2.0D to 5.0D, for example 2.0D to 4.0D, or preferably 2.5D to 3.5D, for example. For hyperopic defocus, he focused images may appear approximately 1.5 mm to 2.5 mm behind of the peripheral retina, in order to be hyperopic by about −2.0D to −5.0D, for example −2.0D to −4.0D, or preferably −2.5D to −3.5D, for example.

In accordance with some embodiments, a soft contact lens 10 comprises projection units which include projection optics and micro-displays as the light source. The micro-displays may comprise an OLED (organic light emitting diode) or an array of micro-LEDs. Light emitted by these displays may be Lambertian. In some embodiments, the micro-display is optically coupled to a micro-optical array that substantially collimates and focuses the light emanating from the micro-display. The micro-display may comprise one or more miniaturized pixels. In some embodiments, the micro-display forms an extended array of pixels, characterized by a pixel size and a pixel pitch, in which the pixel size and the pixel pitch together correspond to a fill factor of the micro-display. As described herein, each of the pixels may have a size within a range from about 2 microns to about 100 microns, and the pixel pitch may range from 10 microns to 1.0 mm, for example. The corresponding fill factor can range from 0.1% to 10%. In some embodiments, the pixel array is optically coupled with a micro-optic array in order to substantially collimate and focus light from the pixels.

The images created by these displays is defocused and may be placed symmetrically in four quadrants of the field of view or of the eye (e.g. nasal-inferior, nasal-superior, temporal-inferior and temporal-superior). The micro displays can be located away from the optical center of the lens by a distance within a range from 1.5 mm to 4.0 mm, preferably 2.5 mm to 3.5 mm. The central optic of the contact lens can be selected to bring the wearer to emmetropia, and may have a diameter within a range 3.0 to 5.0 mm. Each micro-display may be circular, rectangular or arcuate in shape and have an area within a range from 0.01 mm2 to 8.0 mm2, for example within a range from 0.04 mm2 to 8.0 mm2, for example within a range from 1 mm2 to 8 mm2, or preferably within a range from 1.0 mm2 to 4.0 mm2, in some embodiments.

The micro-display can be coupled to and supported with the body of the correction optic such as a contact lens, for example. In some embodiments, the micro-displays are coupled to and supported with one or more of an intraocular lens, a corneal prosthesis, a corneal onlay, or a corneal inlay.

The optical configurations described herein with reference to a contact lens can be similarly used with one or more of an intraocular lens, a corneal prosthesis, a corneal onlay, or a corneal inlay, for example.

In some embodiments, the micro-displays and the micro-optic arrays are mounted immediately adjacent to each other on the same correction optic, separated by a fixed distance in order to project a bundle of rays to the pupil of the eye, at an orientation that it forms a defocused image at a desired location on the retina as described herein. In some embodiments, the one or more projection optics are mounted on or in the one or more correction optics, such that rays from the projection optics are refracted through the correction optics. The correction optics refract the rays from the projection optics to be convergent or divergent as helpful for clear vision, so that the micro-optical array can provide the desired magnitude of additional power that may be plus or minus, depending on the magnitude and sign of the defocus desired. The micro-display may be monochromatic or polychromatic, for example.

In some embodiments, the projected defocused image can be provided by a micro-display comprising a screen comprising one or more of an LCD screen, a screen driven by OLEDS (organic light emitting diodes), TOLEDS, AMOLEDS, PMOLEDS, or QLEDS. The screen may appear to the subject at a far distance of east least 6 meters or more, for example.

Figure 3:
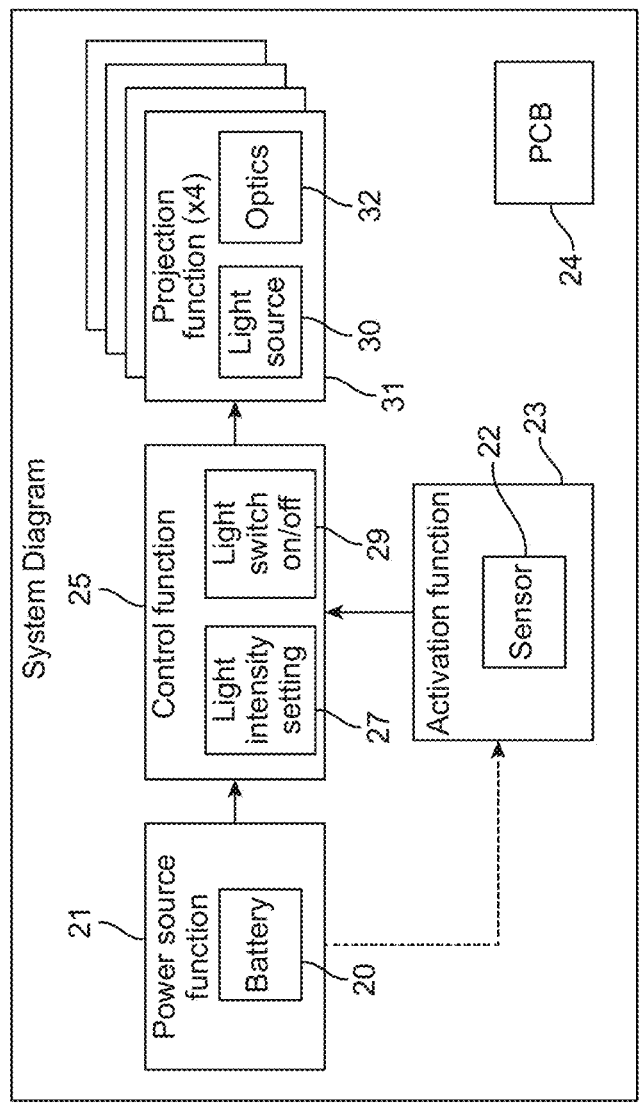
FIG. 3 shows a system diagram for the electrical and mechanical components of the contact lens of FIG. 2, in accordance with some embodiments.

FIG. 3 shows mechanical integration of the function of the components of a retinal stimulation device, such as a contact lens 10 as in FIG. 2. Although reference is made to mechanical integration with a contact lens, similar integration can be performed with any vision device as described herein. These components can be supported with the PCB 24. For example, the power source such as a battery 20 can be mounted on the PCB 24 and coupled to other components to provide a power source function 21. The sensor 22 can be configured to provide an activation function 23. The sensor 22 can be coupled to a processor mounted on the PCB 24 to provide a control function 25 of the contact lens 10. The control function 25 may comprise a light intensity setting 27 and a light switch 29. The processor can be configured to detect signal from the sensor 22 corresponding to an increase in intensity, a decrease in intensity, or an on/off signal from the sensor 22, for example with a coded sequence of signals from the sensor 22. The processor is coupled to the light projection units 18 which can comprise a light source 30 and optics 32 to provide the projection function 31. For example, the processor can be coupled to the plurality of light sources 30 to control each of the light sources 30 in response to user input to the sensor 22.

The retinal stimulation device may comprise global positioning system (GPS) circuitry for determining the location of the wearer, and an accelerometer to measure body movement such as head movement. The retinal stimulation device may comprise a processor coupled to one or more of the GPS or the accelerometer to receive and store measured data. The retinal stimulation device may comprise communication circuitry such as wireless communication circuitry, e.g. Bluetooth or WiFi, or wired communication circuitry, e.g. a USB, in order to transmit data from the device to a remote server, such as a cloud-based data storage system. This transmission of data to the remote server can allow the treatment and compliance of the wearer to be monitored remotely. In some embodiments, the processor comprises a graphics processing unit (GPU). The GPU can be used to efficiently and rapidly process content from the web in order to utilize this content in forming the stimulus as described herein.

The methods and apparatus for retinal stimulation as described herein can be configured in many ways and may comprise one or more attributes to encourage a user to receive therapy. For example, the retinal stimulation as described herein can be combined with a display of a game to encourage a user to wear the treatment device. In some embodiments, the retinal stimulation can be combined with another stimulus, such as an emoji, e.g. a smiley face, to encourage a user to wear the device for treatment. The components of the system may communicate with or receive information from a game or other stimulus to facilitate the retinal stimulation with the game or stimulus.

FIGS. 4A and 4B show a contact lens 10 with supports such as pillars for supporting the electrical and mechanical components in the contact lens. The contact lens 10 is configured to project a defocused image on the retina away from the central field that includes the macula in order to stimulate a change in choroidal thickness as described herein. The contact lens 10 may include a plurality of components, such as projection units 12. Each of the plurality of projection units 12 comprises a light source and one or more optics to focus light in front of the retina as described herein. Each of the optics may comprise one or more of a mirror, a plurality of mirrors, a lens, a plurality of lenses, a diffractive optic, a Fresnel lens, a light pipe or a wave guide. The contact lens 10 may comprise other components, such as a battery and processor system 20 and a sensor 22. The contact lens 10 may comprise a flex printed circuit board (PCB) 24, and a processor can be mounted on the flex PCB 24. The processor can be mounted on the PCB 24 and coupled to the sensor 22 and the plurality of light sources 12. The soft contact lens 10 may also comprise wireless communication circuitry and one or more antennae 41 for electronic communication and for inductively charging the battery 20 of the contact lens 10.

The contact lens my include a body of contact lens material that is a biocompatible material that can encapsulate the components of the soft contact lens 10. The contact lens may also include one or more supports 40 for supporting the components within the contact lens body. For example, the supports may be formed during the fabrication process to hold or suspend the components away from molds used to form the lens body. In this way, uncured lens material is able to flow around the supported components during fabrication. Then, the lens material is cured with the suspended and encapsulated components therein. The processes and structures described herein allow the formation of a contact lens with electromechanical components fully encapsulated within the lens material and may avoid electromechanical components from protruding the lens body. In some embodiments, the material may be a low swell material, such as that described in U.S. Pat. App. Pub. 2008/0291391, titled "Hybrid Contact Lenses Prepared with Expansion Controlled Polymeric Material," filed May 25, 2007. In some embodiments, the contact lens material may be a zero-swell material. The soft contact lens material may comprise any suitable material, such as a hydrogel, a silicone, or other suitable material such as a polymeric material that comprises recurring units selected from the group consisting of (meth)acrylic monomers including linear (siloxanyl)alkyl (meth)acrylates, branched (siloxanyl)alkyl (meth)acrylates, and cyclic (siloxanyl)alkyl (meth)acrylates, silicone-containing (meth)acrylates, fluorine-containing (meth)acrylates, hydroxyl group containing (meth)acrylates, (meth)acrylic acid, N-(meth)acryloylpyrrolidone, (meth) acrylamides, aminoalkyl (meth)acrylates, alkoxy group-containing (meth)acrylates, aromatic group containing (meth)acrylates, glycidyl (meth)acrylate, tetrahydrofurfuryl (meth)acrylate, silicone-containing styrene derivatives, fluorine-containing styrene derivatives, styrene derivatives, and vinyl monomers.

The location of the supports 40 may be configured in many ways. The location of the supports 40 may be determined based on the location of the components within the contact lens 10. For example, the PCB 24 that electrically couples the light sources 12 to the other components may form a concentric ring or a partial concentric ring about the clear central zone 14 of the contact lens. The PCB supports 40a may also be arranged in a concentric ring located about the clear central zone 14 of the contact lens at locations corresponding to the location of the PCB 24. In some embodiments, the supports 40a may be arranged in a circular array with supports at regular angular intervals or with regular spacing between adjacent supports 40a.

In some embodiments, the contact lens 10 may include an antenna 41. The antenna 41 may be located near the outer perimeter of the contact lens 10. In some embodiments, the antenna may form a ring or partial ring proximate the outer perimeter of the contact lens 10. In some embodiments, antenna supports 40b may also be arranged in a concentric ring located proximate the outer perimeter of the contact lens 10 at locations corresponding to the location of the antenna 41. In some embodiments, the supports 40b may be arranged in a circular array with supports at regular angular intervals or with regular spacing between adjacent supports 40b. In some embodiments, the supports are arranged in two concentric rings about the center of the contact lens. A first of the concentric rings supporting the PCB and a second of the concentric rings supporting the antenna.

In some embodiments, the supports 40 may be arranged in pairs, for example supports 40c are arranged in pairs. A pair of supports 40c may be located immediately adjacent to each other. In some embodiments, a first of a pair of supports 40c may be located at a location on a first side of a component and a second of the pair of supports 40c may be located on a second side of a component. For example, in some embodiments, the supports may form hemispherical shapes. A valley or channel may be formed between a pair of adjacent hemispherical supports. The valley or channel may be at a location that corresponds to the location of the component that is to be supported by the support, such as antenna 41.

Although only a single pair of supports 40c are depicted in FIG. 4A, a pair supports may be located at any location that an individual support 40 may be located. For example, the pairs of supports 40c may be arranged in a circular array at regular intervals or at regular spacing between the adjacent pairs of supports 40c in order to support an antenna 41 or PCB 24. In some embodiments, the pairs of supports may be located about any location where a narrow component may be supported.

In some embodiments, supports 40 may be arranged in a two-dimensional array. For example, supports 40d are arranged in a 2×3 two-dimensional array beneath the sensor component 22. A two-dimensional array of supports may be useful in supporting larger components, such as a sensor, a battery, a processor, and other larger components. The supports 40d may be arranged at regular intervals between each other. In some embodiments, the intervals between supports may differ. For example, the two-dimensional array may have columns and rows of supports. The intervals or distance between adjacent columns of supports may vary and may be different than the intervals or distance between adjacent rows of supports. In some embodiments, the interval or distance between adjacent rows of supports may vary and may be different than the intervals or distance between adjacent columns of supports.

In some embodiments, supports 40 may have different sizes and shapes. For example, support 40e has a larger dimension, such as a diameter, than the other supports depicted in FIG. 4A.

In some embodiments, adjacent supports may be separated from each other by a distance. The distance between supports may be between 0.1 mm and 3 mm. In some embodiments, the distance between supports may be less than 2 mm. In some embodiments, the distance between supports may be less than 1 mm. In some embodiments, the distance between supports may be about 0.1 mm, 0.25 mm, 0.5 mm, 0.75 mm, 1.0 mm, 1.25 mm, 1.5 mm, 1.75 mm, or 2 mm.

In some embodiments, the distance between supports may be a relative distance. For example, in some embodiments, the distance between supports may be based on the diameter, height, width, or other dimension of the support. In some embodiments, the supports may be about one half the dimension from each other. In some embodiments, the supports may be between 0.1 and 6.0 dimensions of each other.

In some embodiments, the distance between supports may be measured from the outer perimeter of the adjacent supports. In some embodiments, the distance between supports may be measured from a center of the support.

In some embodiments, the supports may be arranged in differing densities. The density of the supports may be defined by the surface area of the supports as compared to the surface area of the component that the supports support. For example, the supports 40d may be arranged at a first density of less than 10% while the supports may be arranged at a second density of greater than 30%. In some embodiments, the support density may be 100%. In some embodiments, the support density may be between about 10% and less than 100%. In some embodiments, the support density may be between about 30% and about 60%.

In some embodiments, some of the supports may be located in positions within the contact lens that do not correspond to the location of electromechanical components. In some embodiments the ratio supports in locations that correspond to a location of electromechanical components to supports in locations that do not correspond to a location of electromechanical components is greater than 3 to 1. In some embodiments the ratio is preferably greater than 5 to 1 in more preferably greater than 10 to 1 in order to decrease the number of pillars that do not support electromechanical components.

In some embodiments, one or more supports is dimensioned to position a flexible printed circuit board (PCB) with a gap between the flex PCB and a contact lens mold from which the one or more supports extends. The one or more supports may comprise a plurality of supports, in which the gap between the flex PCB and the contact lens mold extends around each of the plurality of supports. In some embodiments, the gap is dimensioned to receive flowable material for curing to form the contact lens body. While the gap can be dimensioned in many ways to receive the flowable material, in some embodiments the gap comprises distance extending from flex PCB toward the contact lens mold and is within a range from 0.010 mm to 0.3 mm, and optionally within a range from 0.040 mm to 0.2 mm. In some embodiments, the gap extends from a surface of the flex PCB to a surface of the contact lens mold from which the support extends. Alternatively or in combination, the gap may extend from the flex PCB to a thin layer of polymer material on the contact lens mold from which the one or more supports extends as described herein.

FIG. 4B shows a cross section of the contact lens with supports of FIG. 4A. As depicted in FIG. 4B, supports 40 may extend from one or both sides of the contact lens 10. In some embodiments, supports may extend from only a side of the contact lens that faces the eye, while in some embodiments, supports may extend from only the side of the contact lens that faces away from the eye. As shown in FIG. 4B, the supports 40 extend from a surface of the contact lens in order to hold or suspend the components of the contact lens, such as the PCB 24, within the contact lens material. In this way, the components are suspended or encapsulated within the contact lens material.

The supports 40 may have a width or diameter 44. The width or diameter 44 may be between about 0.05 mm and about 2.0 millimeters, preferably between about 0.3 mm and about 1 mm. In some embodiments, the diameter or width 44 of the supports 40 may be sized relative to the component that the support supports. For example, in some embodiments, the width or diameter 44 may be equal to or less than the width or diameter of the component. In some embodiments, the width or diameter 44 of the support may be between 20% and 120% of the width of or diameter of the component it is supporting. In some embodiments, the width or diameter 44 of the support may be between 20% and 80% of the width or diameter of the component it is supporting. In some embodiments, the width or diameter of the support may be less than about 100%, 90%, 80%, 70%, 60%, 50%, 40%, 30%, or 20% of the width of the component it is supporting.

The supports 40 may extend from a surface of the contact lens with a height 42. The height of the support may be between 0.010 mm and 0.3 mm. In some embodiments, the height of the support may be between 0.040 mm and 0.2 mm. In some embodiments, the height of the support may be based on the thickness 46 of the contact lens 10. In some embodiments, the height of the support is less than 50% of the thickness of the contact lens 10. In some embodiments, the height of the support is between 20% and 80% of the thickness of the contact lens 10. In some embodiments, the height of the support is between 30% and 70% of the thickness of the contact lens 10. In some embodiments, the height of the support is between 40% and 60% of the thickness of the contact lens 10. In some embodiments, the support extends from at least one of the surfaces of the contact lens with a height of at least 0.02 mm.

In some embodiments, the supports 40 may have a defined volume. The volume of the support may be between about 0.005 uL and 0.5 uL. In some embodiments, the volume of the supports may be between 0.01 uL and 0.1 uL.

In some embodiments, for example for supports arranged in a circular array, the supports may be located an angular distance from each other. For example, in some embodiments, the supports may be located between 10° and 30° from each other. In some embodiments, the supports are located about 10°, about 15°, about 20°, about 25°, about 30°, about 35°, about 40°, or about 45° from each other.

Figure 5B:
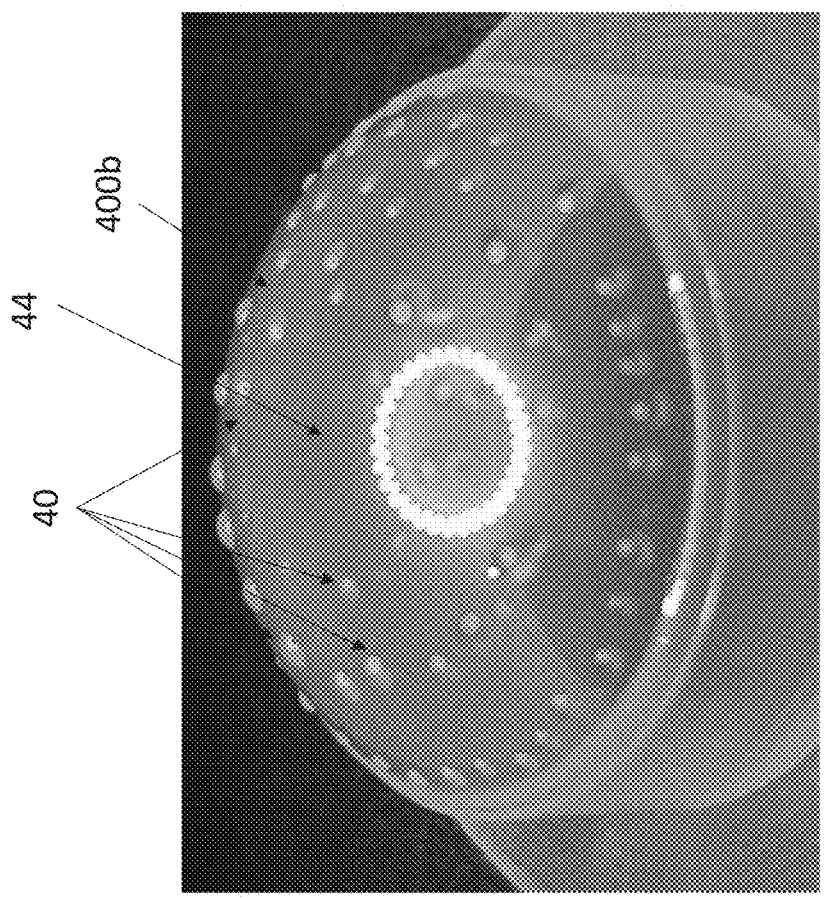
FIGS. 5A, 5B, 5C, 5D, and 5E show supports formed on contact lens molds, in accordance with some embodiments.
Figure 5A:
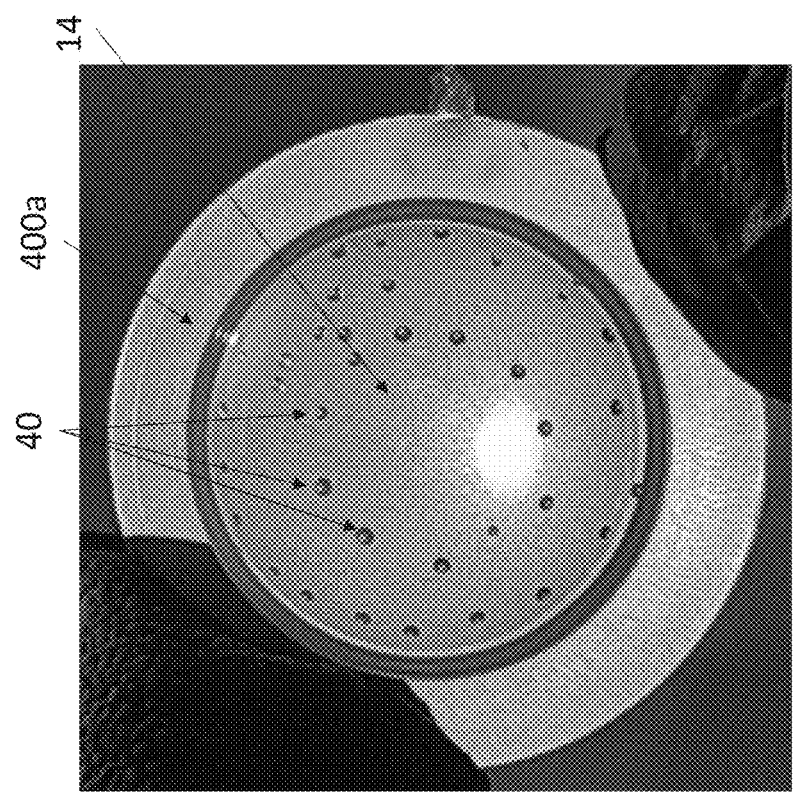

FIGS. 5A, 5B, 5C, 5D, and 5E show supports formed on contact lens molds. FIG. 5A shows a plurality of supports 40 formed on a concave mold 400a. The supports 40 are deposited on the surface of the mold 400a while leaving the central optical zone 14 clear of supports. The supports 40 may be deposited on the mold by any means. For example, in some embodiments, the supports are individually deposited, one at a time, in an automated process. In some embodiments, a computer numerical control machine (CNC) may be programmed to move to the desired locations and dispense a volume of contact lens material onto the mold in order to form the support. In some embodiments, the contact lens material may be deposited via a pipette for other volumetric metering device. In some embodiments, an array of dispensers arranged according to the desired locations of the supports may simultaneously dispense a plurality of supports on the concave mold 400*a*. In some embodiments, a direct fabrication machine, such as a 3D printer, may deposit the contact lens material at the desired locations of the concave mold.

FIG. 5B shows a plurality of supports 40 formed on a convex mold 400*b*. The supports 40 are deposited on the surface of the mold 400*b* while leaving the central optical zone 14 clear of supports. The supports 40 may be deposited on the mold by any means. For example, in some embodiments, the supports are individually deposited, one at a time, in an automated process. In some embodiments, a computer numerical control machine (CNC) may be programmed to move to the desired locations and dispense a volume of contact lens material onto the mold in order to form the support. In some embodiments, the contact lens material may be deposited via a pipette for other volumetric metering device. In some embodiments, an array of dispensers arranged according to the desired locations of the supports may simultaneously dispense a plurality of supports on the convex mold 400*b*.

In some embodiments, a direct fabrication machine, such as a 3D printer, may deposit the contact lens material at the desired locations of the convex mold. In some embodiments, the contact lens material may be an uncured monomer. In some embodiments, in order to facilitate deposition of the contact lens material in the desired locations, the contact lens material may be partially cured.

In some embodiments, the surface tension of the drops and/or the degree of wetting between the contact lens material and the mold may be controlled in order to aid in preventing undesired movement of the deposited contact lens material and an order for the contact lens material to form a meniscus on the mold. In some embodiments, the wetting angle between the contact lens material of the support and the mold is between 10° and 150°. In some embodiments, the wetting angle is between 10° and 90°. In some embodiments, the wetting angle it is less than 90°. In some embodiments, the wetting angle is greater than 10°.

In some embodiments, after the uncured or partially cured contact lens material is deposited onto the mold, the uncured or partially cured contact lens material is put through curing process. In some embodiments, the contact lens material of the supports is fully cured during the curing process. In some embodiments, the contact lens material is partially cured during the curing process. In some embodiments, after curing the supports, the contact lens components are placed on the supports. Partially cured supports may provide greater adhesion between the contact lens components and the supports as compared to fully cured supports thereby aiding in the contact lens fabrication process.

In some embodiments, after curing, a region of slightly decreased strength in the contact lens may be formed at the interface between the pillar and the contact lens body, such that the pillar can be detected. In some embodiments, the pillar can be detected by sectioning the contact lens. Alternatively or in combination, the interface may allow for separation of the pillar from the contact lens body with experimental testing, e.g. with tweezers, although such separation typically will not occur during normal wear and usage of the contact lens. In some embodiments, the region of decreased strength may be formed based on different times of curing of the polymer at the interface, different amounts of cross-linking at the interface between the pillar and the contact lens body, and differing amounts or degrees of curing. For example, the pillars may have been subjected to two curing phases while the rest of the contact lens body may have been subjected to a single curing phase. Alternatively or in combination, the curing of the support prior to the rest of the material, can result in fewer covalent bonds extending across the interface as compared to the bulk polymer material in either the supporting pillars or the contact lens body surrounding the supporting pillars.

Figure 5C:
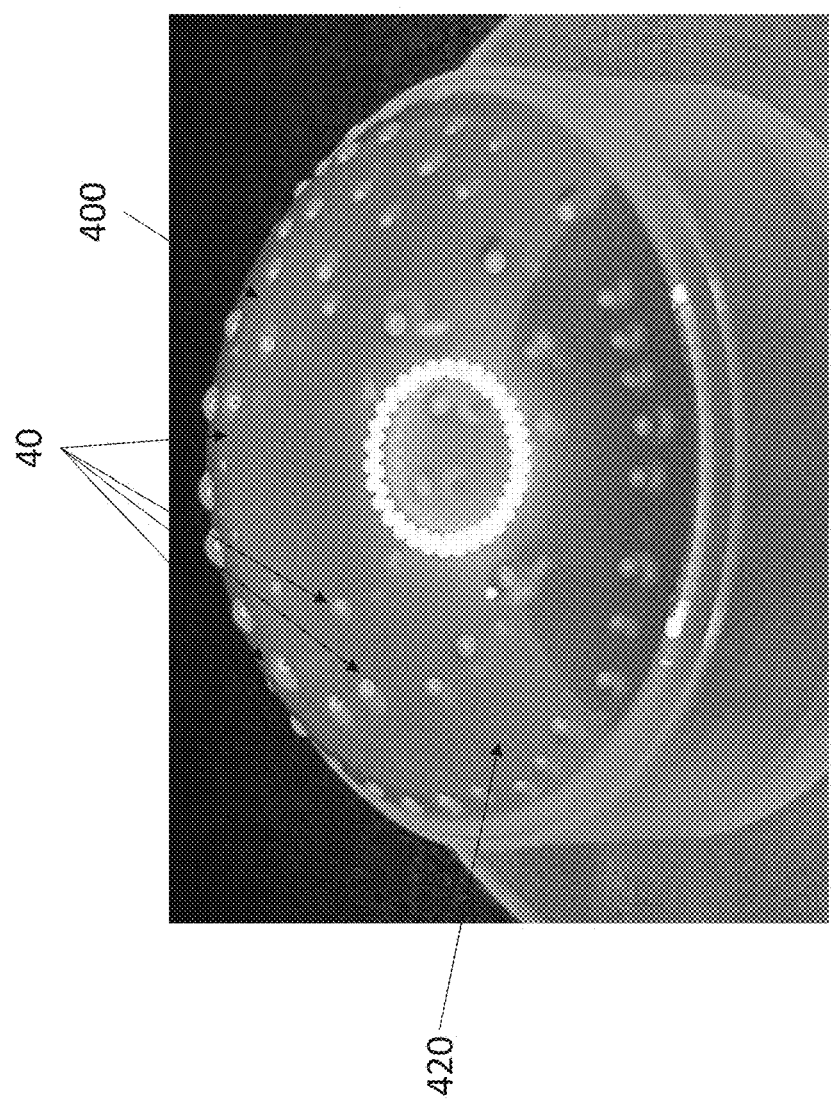
Figure 5D:
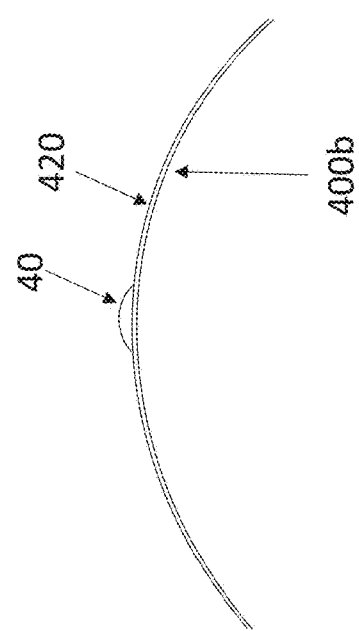

FIGS. 5C and 5D depict a variation of the support fabrication process. In some embodiments, a thin film 420 of contact lens material may be formed on the surface of the mold prior to the formation of the supports 40 on the thin film 420. In some embodiments, the thin film 420 is formed by depositing the contact lens material to the mold and then spinning the mold in order to spread out and thin the contact lens material on the mold 400. The thin layer may be between 0.001 mm and 0.05 mm thick. In some embodiments, the thin layer may be between 0.005 mm and 0.02 mm thick.

After the thin layer contact lens materials formed on the mold, the thin layer may be cured. In some embodiments, the thin layer 420 may be fully cured. In some embodiments, the thin layer 420 may be partially cured.

After curing the thin layer 420, supports 40 may be deposited onto the thin layer 420 contact lens material. The supports 40 may be deposited on the thin layer 420 by any means. For example, in some embodiments, the supports are individually deposited, one at a time, in an automated process. In some embodiments, a computer numerical control machine (CNC) may be programmed to move to the desired locations and dispense a volume of contact lens material onto the thin layer 420 in order to form the support. In some embodiments, the contact lens material may be deposited via a pipette or other volumetric metering device. In some embodiments, an array of dispensers arranged according to the desired locations of the supports may simultaneously dispense a plurality of supports on the thin layer 420.

In some embodiments, a direct fabrication machine, such as a 3D printer, may deposit the contact lens material at the desired locations of the thin layer 420. In some embodiments, the contact lens material may be an uncured monomer. In some embodiments, in order to facilitate deposition of the contact lens material in the desired locations, the contact lens material may be partially cured.

In some embodiments, the surface tension of the drops and/or the degree of wetting between the contact lens material and the thin layer 420 may be controlled in order to aid in decreasing undesired movement of the deposited contact lens material and an order for the contact lens material to form a meniscus on the thin layer 420. In some embodiments, the wetting angle is between 10° and 150°. In some embodiments, the wetting angle is between 10° and 90°. In some embodiments, the wetting angle it is less than 90°. In some embodiments, the wetting angle is greater than 10°.

In some embodiments, after the uncured or partially cured contact lens material is deposited onto the thin layer 420 the uncured or partially cured contact lens material is put through curing process. In some embodiments, the contact lens material of the supports is fully cured during the curing process. In some embodiments, the contact lens material is partially cured during the curing process.

Figure 5E:
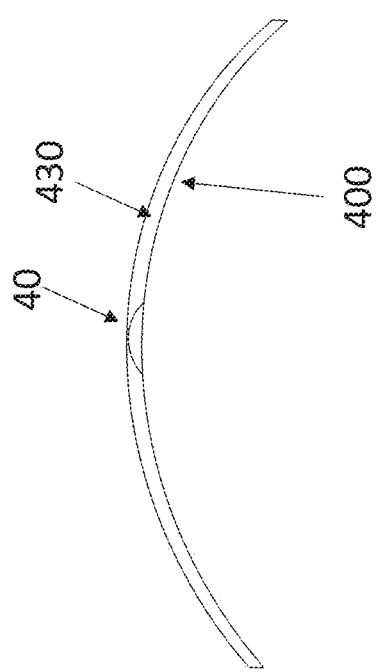

FIG. 5E shows a variation of the support fabrication process. In some embodiments, a layer 430 of contact lens material may be formed on the surface of the mold prior to the formation of the supports 40. In some embodiments, the layer 430 is formed by depositing the contact lens material to the mold and then spinning the mold in order to spread out and thin the contact lens material on the mold 400 to a desired thickness. The thickness of the layer 430 may be the same as the desired height of the supports 40.

After the layer of contact lens material is formed on the mold, the layer may be selectively cured. In some embodiments, the layer 430 may be selectively fully cured. In some embodiments, the layer 430 may be selectively partially cured. The selectively cured portions of the layer 430 may form the supports of the contact lens. The selected curing process may be carried out using a mask, for example, as shown and described with respect to FIGS. 7A and 7B. In some embodiments, the uncured contact lens material may be washed off the mold 400. In some embodiments, the uncured contact lens material may remain on the mold 400.

FIGS. 6A and 6B show a mask 600 that may be used in forming supports 40. The mask 600 may include a mask body 608 with a plurality of wells 606 formed through the mask body 608. A well 606 may be an aperture extending through the body 608 of the mask 600. For example, in some embodiments, a well 606 may extend from a first surface of the mask to a second surface of the mask to form an aperture through the body 608 of the mask 600. In some embodiments, the wells 606 are arranged according to the position of the components of the contact lens 10. For example, in some embodiments, wells 606 may form a plurality of arcuate apertures through the mask to form supports to support an antenna. In some embodiments, the wells may be shaped according to the shape of a PCB or light sources in order to support the PCB and light sources. In some embodiments, the wells may have a shape that corresponds to the shape of other components such as sensors, processors, batteries, and other components. In some embodiments, the dimensions of the wells correspond to a projection of the contact lens components on the contact lens. In some embodiments, the dimensions of the wells are smaller than a projection of the contact lens components on the contact lens.

While the mask 600 depicted in FIG. 6A has wells that correspond to the shape of the components of the contact lens. In some embodiments, the wells may have other shapes and locations. For example, the wells may have shapes and locations that correspond to the desired shape and location of supports 40 as shown and described herein, for example with respect to FIG. 4A.

In some embodiments, the wells 606 may be arranged in a circular array at regular angular intervals or with regular spacing between adjacent wells 606. In some embodiments, the wells 606 are arranged in two concentric rings about the center of the mask 600. A first of the concentric rings for forming supports for supporting the PCB and a second of the concentric rings for forming supports for supporting the antenna.

In some embodiments, the wells 606 may be arranged in pairs. A pair of wells 606 may be located immediately adjacent to each other. In some embodiments, wells 606 are arranged in a 2×3 two-dimensional array for supporting a sensor component 22. The wells 606 may be arranged at regular intervals between each other. In some embodiments, the intervals between wells 606 may differ. For example, the two-dimensional array may have columns and rows of wells 606. The intervals or distance between adjacent columns of wells 606 may vary and may be different than the intervals or distance between adjacent rows of wells 606. In some embodiments, the interval or distance between adjacent rows of wells 606 may vary and may be different than the intervals or distance between adjacent columns of wells 606.

In some embodiments, adjacent wells 606 may be separated from each other by a distance. The distance between supports may be between 0.1 mm and 3 mm. In some embodiments, the distance between wells 606 may be between less than less than 2 mm. In some embodiments, the distance between wells 606 may be less than 1 mm. In some embodiments, the distance between wells 606 may be about 0.1 mm, 0.25 mm, 0.5 mm, 0.75 mm, 1.0 mm, 1.25 mm, 1.5 mm, 1.75 mm, or 2 mm.

In some embodiments, the distance between wells 606 may be a relative distance. For example, in some embodiments, the distance between wells 606 may be based on the diameter, height, width, or other dimension of the wells 606. In some embodiments, the wells 606 may be a distance of about one half the dimension from each other. In some embodiments, the wells 606 may be between 0.1 and 3.0 dimensions of each other.

In some embodiments, the distance between wells 606 may be measured from the outer perimeter of the adjacent wells 606. In some embodiments, the distance between wells 606 may be measured from a center of the wells 606.

In some embodiments, the wells 606 may be arranged in differing densities. For example, the wells 606 may be arranged at a first density of less than 10% while other wells 606 may be arranged at a second density of greater than 30%. In some embodiments, the wells 606 density may be between about 10% and less than 100%. In some embodiments, the wells 606 density may be between about 30% and about 60%.

The wells 606 may have a width or diameter. The width or diameter may be between about 0.05 mm and about 2.0 millimeters, preferably between about 0.3 mm and about 1 mm. In some embodiments, the diameter or width of the wells 606 may be sized relative to the component that a support formed from the wells will support. For example, in some embodiments, the width or diameter 44 may be equal to or less than the width or diameter of the component. In some embodiments, the width or diameter of the wells 606 may be between 20% and 120% of the width of or diameter of the component a support formed from the well will support. In some embodiments, the width or diameter of the wells 606 may be between 20% and 80% of the width or diameter of the component formed in the will support. In some embodiments, the width or diameter of the wells 606 may be less than about 100%, 90%, 80%, 70%, 60%, 50%, 40%, 30%, or 20% of the width of the component formed from the well will support.

The wells 606 may have a depth 610. The depth 610 of the well may define the height a support formed within the well. The depth of the well may be between 0.010 mm and 0.3 mm. In some embodiments, the depth 610 of the well 606 may be between 0.040 mm and 0.2 mm. In some embodiments, the depth 610 of the wells 606 may be based on the thickness of the contact lens 10. In some embodiments, the depth 610 of the wells 606 is less than 50% of the thickness of the contact lens 10. In some embodiments, the depth 610 of the wells 606 is between 20% and 80% of the thickness of the contact lens 10. In some embodiments, the depth 610 of the wells 606 is between 30% and 70% of the thickness of the contact lens 10. In some embodiments, the depth 610 of the wells 606 is between 40% and 60% of the thickness of the contact lens 10. In some embodiments, the depth 610 of the wells 606 is at least 0.02 mm.

In some embodiments, the wells 606 may have a defined volume. The volume of the wells 606 may be between about 0.005 uL and 0.5 uL. In some embodiments, the volume of the wells 606 may be between 0.01 uL and 0.1 uL.

In some embodiments, fabricating supports using a mask, such as the mask 600, may start by placing the mask 600 on a mold, such as any of the molds described herein. Contact lens material may then be deposited within the wells 606 of the mask body 608. After the contact lens material is deposited within the well 606 the contact lens material may be cured. In some embodiments, the contact lens material may be fully cured. In some embodiments, the contact lens material may be partially cured. In some embodiments, the contact lens material is at least partially cured such that it adheres to the mold more strongly than it adheres to the mask body 608. By only curing the contact lens material such that it adheres to the mold more strongly than it adheres to the mask body, the mask body may be removed from the mold while the supports formed within the wells remain on the mold.

In some embodiments, the mask is inserted into a concave mold while in some embodiments, the mask is placed on a convex mold.

FIGS. 7A and 7B show a mask 700 that may be used in forming supports 40. The mask 700 may include a mask body 708 with a plurality of apertures 706 formed through the mask body 708. In some embodiments, an aperture 706 may extend from a first surface of the mask to a second surface of the mask to form the aperture through the body 708 of the mask 700. In some embodiments, the mask body 708 is configured to prevent curing radiation, such as visible or ultraviolet light, from passing though body 708 while the apertures 706 transmit curing radiation. In some embodiments, the apertures are empty. In some embodiments, the apertures may be covered or filed with material that transmits curing radiation, such as ultraviolet light.

In some embodiments, the apertures 706 are arranged according to the position of the components of the contact lens 10. For example, in some embodiments, apertures 706 may form a plurality of arcuate apertures through the mask body for the formation of supports to support an antenna. In some embodiments, the apertures may be shaped according to the shape of a PCB and light sources, in order to support the PCB and light sources. In some embodiments, the apertures may have a shape that corresponds to the shape of other components such as sensors, processors, batteries, and other components. In some embodiments, the dimensions of the apertures correspond to a projection of the contact lens components on the contact lens. In some embodiments, the dimensions of the apertures are smaller than a projection of the contact lens components on the contact lens.

While the mask 700 depicted in FIG. 7A has apertures that correspond to the shape of the components of the contact lens. In some embodiments, the apertures may have other shapes and locations. For example, the apertures may have shapes and locations that correspond to the desired shape and location of supports 40 as shown and described herein, for example with respect to FIG. 4A.

In some embodiments, the apertures 706 may be arranged in a circular array at regular angular intervals or with regular spacing between adjacent apertures 706. In some embodiments, the apertures 706 are arranged in two concentric rings about the center of the mask 700. A first of the concentric rings for forming supports for supporting the PCB and a second of the concentric rings for forming supports for supporting the antenna.

In some embodiments, the apertures 706 may be arranged in pairs. A pair of apertures 706 may be located immediately adjacent to each other. In some embodiments, apertures 706 are arranged in a 2×3 two-dimensional array for supporting a sensor component 22. The apertures 706 may be arranged at regular intervals between each other. In some embodiments, the intervals between apertures 706 may differ. For example, the two-dimensional array may have columns and rows of apertures 706. The intervals or distance between adjacent columns of apertures 706 may vary and may be different than the intervals or distance between adjacent rows of apertures 706. In some embodiments, the interval or distance between adjacent rows of apertures 706 may vary and may be different than the intervals or distance between adjacent columns of apertures 706.

In some embodiments, adjacent apertures 706 may be separated from each other by a distance. The distance between supports may be between 0.1 mm and 3 mm. In some embodiments, the distance between apertures 706 may be between less than less than 2 mm. In some embodiments, the distance between apertures 706 may be less than 1 mm. In some embodiments, the distance between apertures 706 may be about 0.1 mm, 0.25 mm, 0.5 mm, 0.75 mm, 1.0 mm, 1.25 mm, 1.5 mm, 1.75 mm, or 2 mm.

In some embodiments, the distance between apertures 706 may be a relative distance. For example, in some embodiments, the distance between apertures 706 may be based on the diameter, width, or other dimension of the apertures 706. In some embodiments, the distance may be based on a height of a support to be formed with the aperture. In some embodiments, the apertures 706 may be a distance of about one half the dimension from each other. In some embodiments, the apertures 706 may be between 0.1 and 3.0 dimensions of each other.

In some embodiments, the distance between apertures 706 may be measured from the outer perimeter of the adjacent apertures 706. In some embodiments, the distance between apertures 706 may be measured from a center of the apertures 706.

In some embodiments, the apertures 706 may be arranged in differing densities. For example, the apertures 706 may be arranged at a first density of less than 10% while other apertures 706 may be arranged at a second density of greater than 30%. In some embodiments, the apertures 706 density may be between about 10% and less than 100%. In some embodiments, the apertures 706 density may be between about 30% and about 60%.

The apertures 706 may have a width or diameter. The width or diameter may be between about 0.05 mm and about 2.0 millimeters, preferably between about 0.3 mm and about 1 mm. In some embodiments, the diameter or width of the apertures 706 may be sized relative to the component that a support formed from the apertures will support. For example, in some embodiments, the width or diameter may be equal to or less than the width or diameter of the component. In some embodiments, the width or diameter of the apertures 706 may be between 20% and 120% of the width of or diameter of the component a support formed from the aperture will support. In some embodiments, the width or diameter of the apertures 706 may be between 20% and 80% of the width or diameter of the component formed in the will support. In some embodiments, the width or diameter of the apertures 706 may be less than about 100%, 90%, 80%, 70%, 60%, 50%, 40%, 30%, or 20% of the width of the component formed from the aperture will support.

In some embodiments, fabricating supports using a mask, such as the mask 700, may start by depositing a layer 420 of contact lens material on the mold 400. In some embodiments, depositing the layer 420 of contact lens material on the mold 400 includes spin forming the material on the mold in order to spread out and thin the contact lens material to a desired thickness. Then, the mask 700 is placed between a curing radiation source, such as a UV light source, and the uncured contact lens material. The curing radiation source is then activated to emit curing radiation, such as UV or visible light 720. The UV light 720 passes through the apertures 708 and selectively cures unmasked portions 722 of the layer 420 of contact lens material to form supports 40. In some embodiments, the contact lens material may be partially cured at supports 40. In some embodiments, the contact lens material is fully cured at supports 40. In some embodiments, after at least partially curing the contact lens material at the selected location 722, the uncured contact lens material that was not exposed to curing radiation is washed off the mold. In some embodiments, the uncured contact lens material that was not exposed to curing radiation is not washed off the mold and the components placed on both the at least partially cured supports 40 and the uncured material of layer 720.

The light 720 can be configured in many ways, and may comprise any suitable wavelength such as visible or ultraviolet light, or other wavelengths of light, and the electromagnetic radiation may comprise other wavelengths of electromagnetic radiation. In some embodiments, the light 720 comprises a substantially collimated beam of light to decrease blurring at the edges of the supports 40 corresponding to the edges of the apertures of the mask. Alternatively or in combination, the beam of light may comprise a low divergence beam, for example with a divergence of no more than about 10 milliradians, to allow the beam of light to be focused substantially to a point on the male side of the contact lens mold or the female side of the contact lens, for example. While the mask is show proximate an external surface of the mold in FIG. 7B, alternatively the mask can be imaged onto the layer 720 by use of one or more suitable lenses between the layer 720 and the mask.

Figure 8:
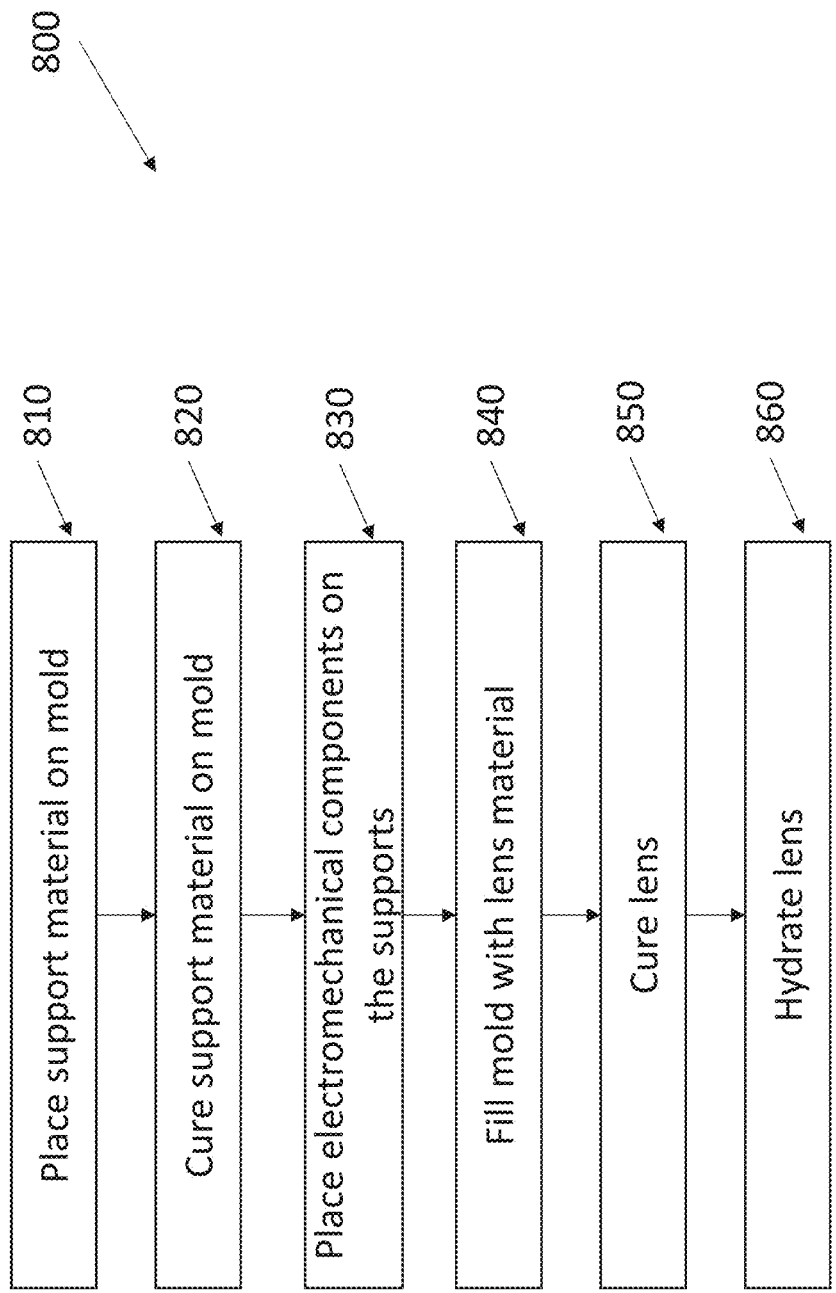
FIG. 8 shows a method of fabricating a contact lens, in accordance with some embodiments.

FIG. 8 shows a method 800 for fabricating a contact lens. The process may start at step 810 where support material is placed on a mold. After the support material placed on the mold the process may continue to step 820 where the support material is cured on the mold. In some embodiments, at step 830 electromechanical components are placed on the cured support material that forms the supports. At step 840 the mold is filled with lens material. After filling the mold with lens material, at step 850 the lens material is cured. In some embodiments, at step 860 lens cured lens material is hydrated and the completed contact lens is removed from the mold.

In more detail, at step 810 the support material is placed on a mold. The support material may be contact lens material, such as a low or zero-swell contact lens material. In some embodiments, the contact lens material may have a swell of between 0% and 2%. The swell of a material refers to the change in volume of the material between a cured and non-hydrated state and dehydrated state.

Placing or depositing support material on a mold may be accomplished in many ways. For example, in some embodiments, a layer of contact lens material may be spin deposited onto the contact lens mold in order to cover the mold, as discussed herein with respect to FIGS. 5C, 5D, 5E, and 7B.

In some embodiments, depositing support material on the mold may include depositing discrete volumes of material on the mold. For example, as shown and described herein with respect to FIGS. 5A and 5B. The supports material may be deposited on the surface of the mold while leaving the central optical zone clear of support material. In some embodiments, the supports are individually deposited, one at a time, in an automated process. In some embodiments, a computer numerical control machine (CNC) may be programmed to move to the desired locations and dispense a volume of contact lens material onto the mold in order to form the support. In some embodiments, the contact lens material may be deposited via a pipette or other volumetric metering device. In some embodiments, an array of dispensers arranged according to the desired locations of the supports may simultaneously dispense a plurality of supports on the concave mold. In some embodiments, a direct fabrication machine, such as a 3D printer, may deposit the contact lens material at the desired locations of the concave mold. In some embodiments, the deposited contact lens material may be an uncured monomer. In some embodiments, in order to facilitate deposition of the deposited contact lens material in the desired locations, the contact lens material may be partially cured before it is deposited on the mold.

In some embodiments, prior to depositing the contact lens support material on the mold, a mask is placed on or in the mold. The mask may have wells, such as shown and described with respect to the mask depicted in FIGS. 6A and 6B. Depositing the contact lens support material on the mold may include filling the wells of a mask with the contact lens material, as described herein.

In some embodiments, depositing the support material on the mold may include first depositing a thin layer of contact lens material on the mold and then spin forming the thin layer contact lens material which may then be at least partially cured, as described herein, for example with respect to FIGS. 5C and 5D. After curing the thin layer, supports may be deposited onto the thin layer of contact lens material. The supports may be deposited on the thin layer by any means. For example, in some embodiments, the supports are individually deposited, one at a time, in an automated process. In some embodiments, a computer numerical control machine (CNC) may be programmed to move to the desired locations and dispense a volume of contact lens material onto the thin layer in order to form the support. In some embodiments, the contact lens material may be deposited via a pipette for other volumetric metering device. In some embodiments, an array of dispensers arranged according to the desired locations of the supports may simultaneously dispense a plurality of supports on the thin layer.

In some embodiments, a direct fabrication machine, such as a 3D printer, may deposit the contact lens material at the desired locations of the thin layer. In some embodiments, the contact lens material may be an uncured monomer. In some embodiments, in order to facilitate deposition of the contact lens material in the desired locations, the contact lens material may be partially cured.

At step 820 the support material may be cured on the mold. In some embodiments, support material that has been deposited on the mold may be at least partially cured. The curing process may include exposing the support material to light such as UV radiation, heat, a combination of heating and light such as UV radiation, or other curing process. In some embodiments, a UV light source projects UV light onto the support material to cure the supports. In some embodiments, the supports may be partially cured such that the supports remain in place while uncured support material is rinsed or washed off of the mold. In some embodiments, the supports may be at least partially cured that the uncured support material is not rinsed or washed off of the mold.

In some embodiments, prior to exposing the support material to UV radiation, a mask is placed between the UV light source and the support material in order to selectively cure the supports, as described herein. In some embodiments, for example those with a mask that includes wells, after curing the support material, the mask is removed from the mold while the cured contact lens material remains attached to the mold.

At step 830 electromechanical components are placed on the supports. In some embodiments, the electromechanical components are assembled together and then deposited onto the supports. In some embodiments, prior to placing the electromechanical components onto the supports, the electromechanical components may be pre-formed into a desired shape. For example, the electromechanical contact lens components may be pre-formed into a curved shape that matches the curve shape of the contact lens. Pre-forming the electromechanical components may include placing the electromechanical contact lens components between two curved jigs which press the contact lens components into a curved shape. In some embodiments, the electromechanical contact lens components are subjected to heating, for example at 100° for one hour, while placed between the two curved jigs in order to set the curved shape in the contact lens components.

In some embodiments, a pick and place machine may be used to place the contact lens components onto the supports. In some embodiments, a CNC machine may be used to place the contact lens components onto the supports. In some embodiments, the contact lens components may be manually placed onto the supports.

At step 840 the mold is filled with lens material. The mold may be filled with additional contact lens material. The contact lens material may be the same material used for the supports. In some embodiments, a pipette for other volumetric metering device dispenses a preselected amount of contact lens material into the mold. In some embodiments, filling the mold with contact lens material, the contact lens material and mold may be subject to vibration in order to reduce or remove potential air pockets within the contact lens material. In some embodiments, the mold is a first mold and defines a first exterior surface of the contact lens. In some embodiments, a second mold is placed over the contact lens material on or within the first mold in order to define a second exterior surface of the contact lens. In some embodiments, the first mold defines a concave surface of the contact lens and the second mold defines a convex surface of the contact lens. In some embodiments, the first mold defines a convex surface of the contact lens and the second mold defines a concave surface of the contact lens.

At step 850 the lens material is cured. The curing process may include exposure to light such as UV radiation, heat, a combination of heating and light such as UV radiation, or other curing process. In some embodiments, a UV light source projects UV light onto the support material to cure the contact lens material. In some embodiments, the contact lens material may be exposed to UV radiation for about 15 seconds, about 30 seconds, about 45 seconds, about 60 seconds, or about 75 seconds. In some embodiments, the lens material may be exposed to UV radiation for between 30 seconds and 90 seconds. In some embodiments, the contact lens material may be exposed to UV radiation for between 45 seconds and 75 seconds.

At step 860 lens material is hydrated. In some embodiments, the cured contact lens may be hydrated. In some embodiments, the cured contact lens is hydrated before it is removed from the mold. Hydrating the contact lens within the mold may aid in removing the advocated contact lens from the mold. In some embodiments, the cured contact lens is removed from the mold and then hydrated.

Although FIG. 8 shows a method 800 for fabricating a contact lens, in accordance with some embodiments, one of ordinary skill in the art will recognize many variations and adaptations. For example, the steps can be performed in any order, some of the steps omitted, and some of the steps repeated. Also, some of the steps may comprise sub-steps of other steps.

Figure 9:
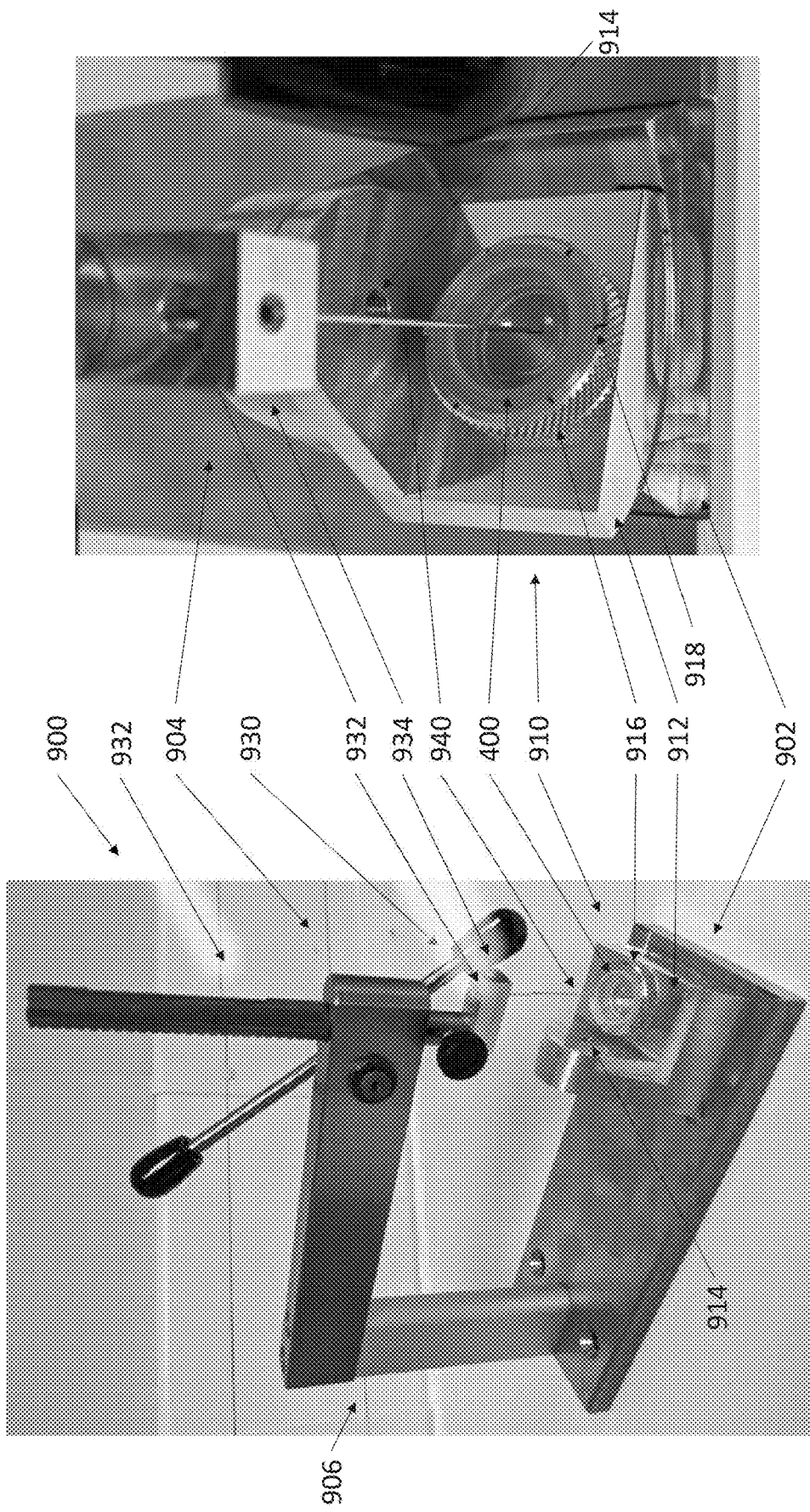
FIGS. 9A and 9B depict an apparatus for depositing pillars on a mold, in accordance with some embodiments.

FIGS. 9A and 9B depict an apparatus 900 for depositing pillars on a contact lens mold. In some embodiments, the location of deposition remains substantially fixed, and the contact lens mold is one or more of rotated or translated to deposit pillars at a plurality of different locations on the contact lens mold. The apparatus 900 may include a base portion 902 that is coupled to a dispensing portion 904 via an arm 906. The base portion 902 is configured to hold and position a contact lens mold 400. The base portion provides at least two rotational degrees of freedom to allow the contact lens mold 400 to be positioned appropriately beneath the dispenser portion 904 for the deposition of material on the contact lens mold 400.

A first rotational degree of freedom of the base portion may be provided by a swiveling or pivoting platform 912. The platform 912 may be rotationally coupled to the base portion 902 along an axis of rotation 914. The axis of rotation 914 provides the first rotational degree of freedom. The axis of rotation 914 may be perpendicular to an axis of deposition, such as the axis along which the dispensing portion 904 may translate or z-axis along which the dispensing conduit 940 extends. In some embodiments, a distance between the axis of rotation 914 and the surface of the mold 400 may be the same as the radius of curvature of a surface of the mold 400, such as the inner surface of the mold 400. In this way, a distance between the surface of the mold and the dispensing conduit 940 may be maintained when the platform 912 is rotated about the axis of rotation 914. In some embodiments, the distance between the surface of the mold 400 and the surface of the mold 400 may be greater than the radius of curvature of the contact lens.

A second rotational degree of freedom of the base portion may be provided by a contact lens holder 916. The contact lens mold holder 916 may be rotationally coupled to the pivoting platform 912 to allow the contact lens mold holder 916 to rotate about an axis that is perpendicular to the rotational axis 914 of the pivoting platform 912. The second rotational degree of freedom allows the contact lens mold 400 to be rotated beneath the dispensing conduit 940. In some embodiments, during use the contact lens mold 400 is positioned with respect to the dispensing conduit such that the dispensing conduit is located at a radial distance from the center of the contact lens mold 400. Then, in some embodiments, the contact lens mold may be rotated about the second rotational axis in order to position the dispensing conduit 940 at concentric locations on the contact lens mold about the center of the contact lens mold without further movement of the base portion 912 about the first rotational axis 914.

In some embodiments, the contact lens 916 may include markings or indications 918. The markings 918 may indicate a location for dispensing or applying the contact lens material onto the contact lens mold for forming a pillar. For example, the apparatus 900 includes six markings 918 that mark the rotational locations for depositing the pillars on the mold 400. In some embodiments, the markings 918 may be physical detents or other mechanical indexing structures that releasably hold the at the indicated rotational locations.

The dispensing portion 904 may include a movable head portion 934. The head portion 934 may be configured to translate along an axis perpendicular to the rotational axis 914. A rack and pinion system 932 connected to a shaft may facilitate the translation of the dispensing portion 914 and the movable head portion 934. The translation axis may be parallel to or coincide with the length of the shaft of the rack and pinion system 932. Translation of the movable head portion 934 allows the end of the dispensing conduit 940 to be positioned on or near the surface of the contact lens mold 400. In some embodiments, the end of the dispensing conduit 940 may be positioned a distance from the contact lens mold that is less than or equal to the height of a pillar. In some embodiments the end of the dispensing conduit 940 may be positioned a distance of less than half the height of a pillar.

In some embodiments, a handle 930 may the coupled to the pinion of the rack and pinion system. Movement or rotation of the handle may cause rotation of the pinion and translation of the rack which may result in translation of the movable head portion 934.

In some embodiments the dispensing conduit 940 may be a needle, a hollow tube, or other elongated hollow structure. In some embodiments, an internal diameter of the dispensing conduit 940 may be less than or equal to the diameter of a pillar. In some embodiments, the internal diameter of the dispensing conduit 940 may be less than half the diameter of a pillar. In some embodiments, the internal diameter of the conduit may be between about 0.01 mm and about 0.5 mm.

The head portion 934 may include a fluid intake port 932 vertically coupled to a dispensing conduit 940. The fluid intake port 932 may be a reservoir that feeds the dispensing conduit 940 through gravity or capillary action. In some embodiments, the fluid intake port 932 may include or otherwise the be fluidically coupled to a pressurized fluid reservoir for holding and dispensing contact lens material for fabricating pillars.

Although reference is made to apparatus 900 comprising a handle, this apparatus may comprise an at least partially automated robotic apparatus configured with one or more robotic components, such as linkages and motors to move the components, and these movable components can be controlled with a processor configured with instructions to deposit pillars as described herein.

Figure 10:
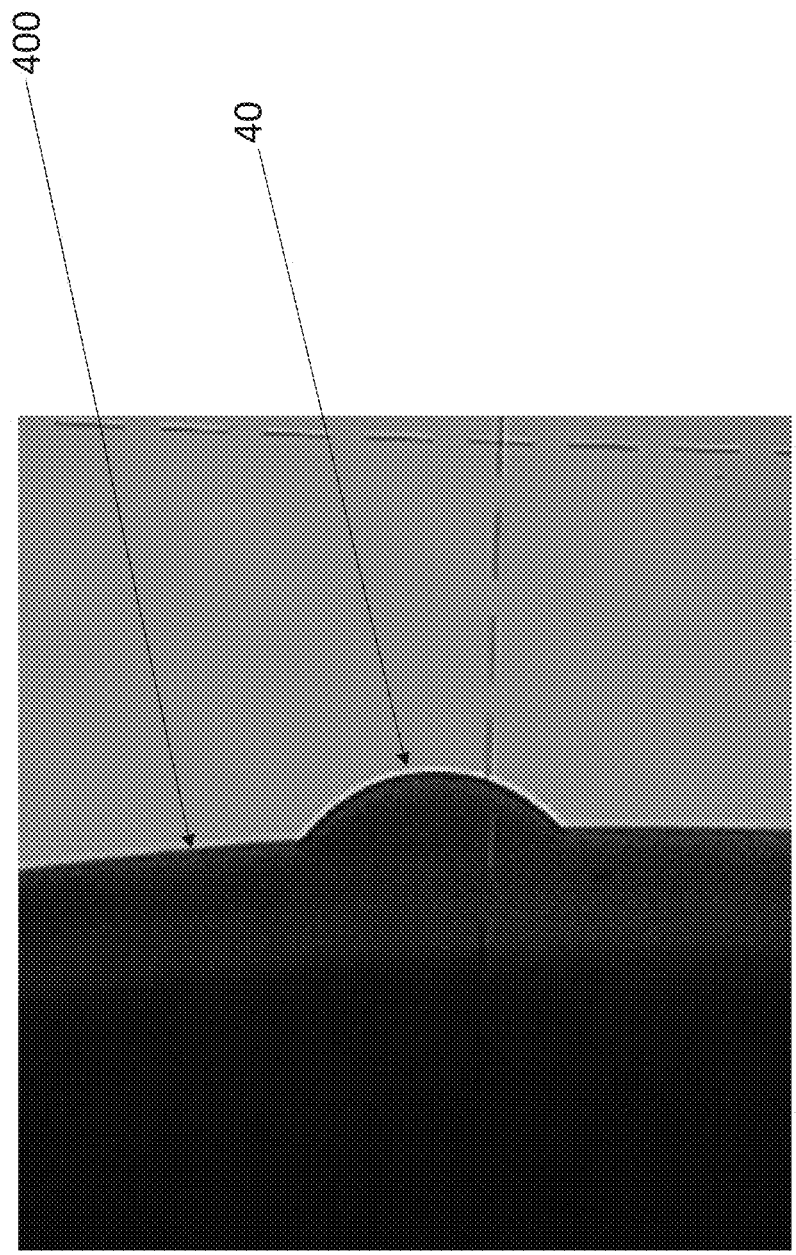
FIG. 10 shows a support formed on a mold, in accordance with some embodiments.

FIG. 10 shows an image of in experimental support 40 formed according to the systems and methods discussed herein. The support 40 is shown on a mold 400 after removal of uncured support material.

Figure 11:
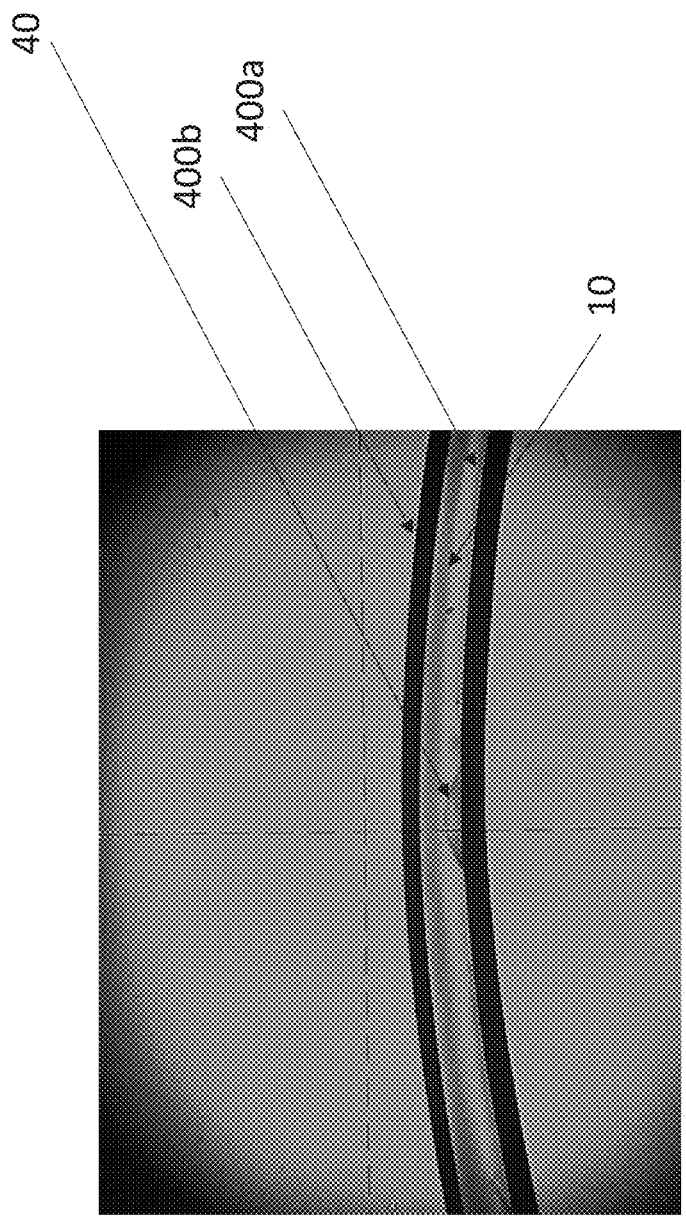
FIG. 11 shows a fabricated contact lens with a support, in accordance with some embodiments.

FIG. 11 shows an image of an experimental contact lens 10 with supports formed according to the systems and methods discussed herein. The contact lens 10 is shown before removal from the mold. The contact lens 10 is encapsulated between a convex mold 400a and a concave mold 400. No electromechanical components are encapsulated within the experimental contact lens 10. The support is shown extending from the concave surface of the contact lens with a height of about one half the thickness of the contact lens.

Figure 12:
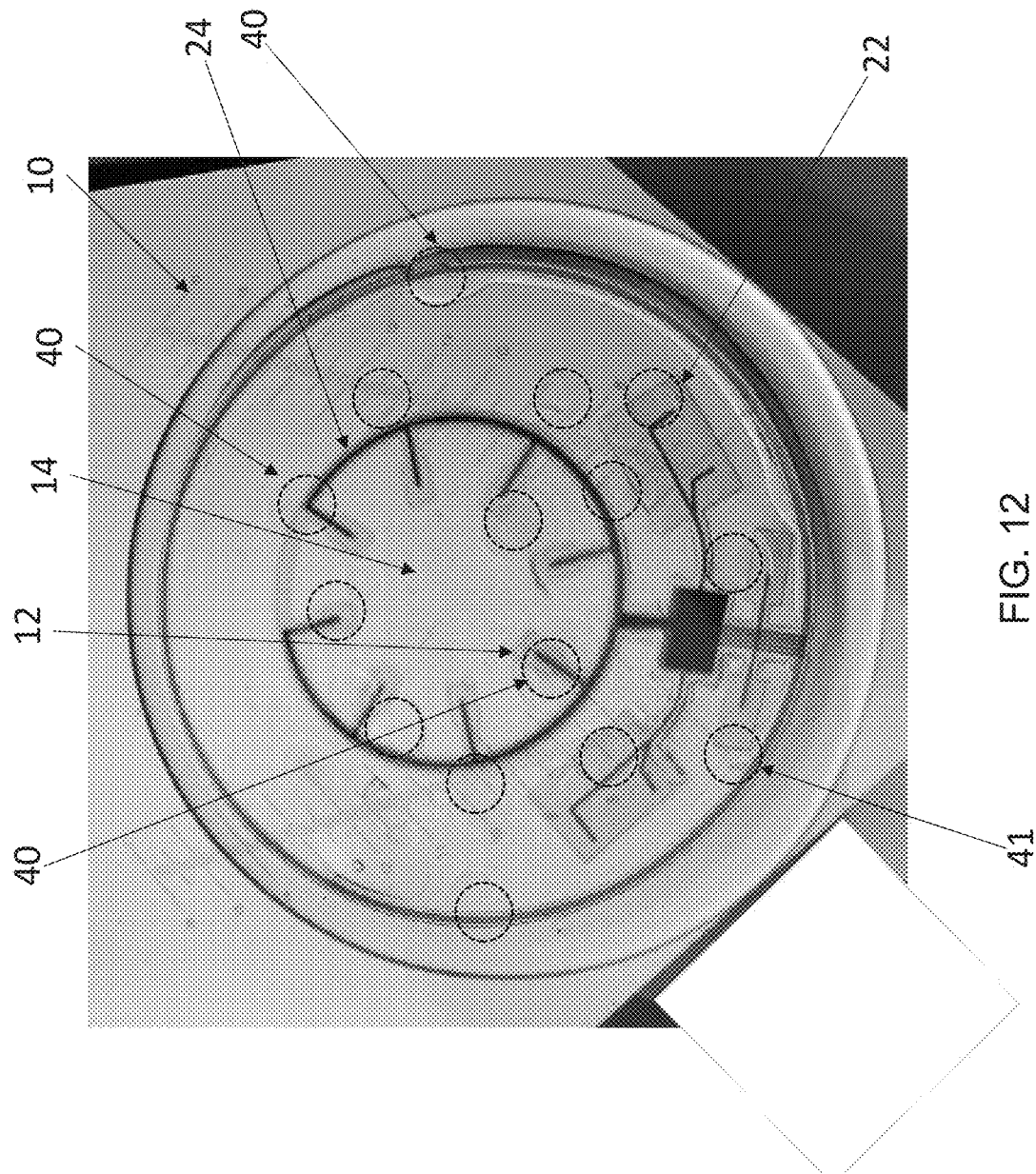
FIGS. 12 and 13 show a fabricated contact lens with supports and mechanical and electrical components therein, in accordance with some embodiments.
Figure 13:
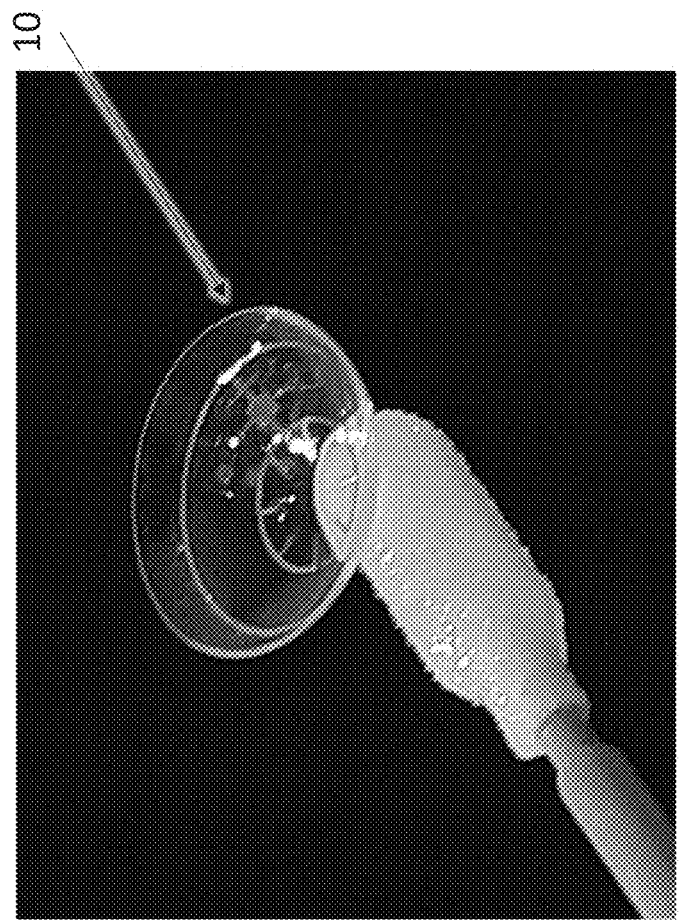

FIGS. 12 and 13 show an experimental contact lens 10 formed with electromechanical components encapsulated within the contact lens 10 and supported by a plurality of supports. The supports 40 are shown supporting various portions of the electromechanical components. For example, the contact lens 10 includes supports that support the antenna 41, the sensors 22, the PCB 24, and the light sources 12. The contact lens 10 includes no supports within the clear central portion 14 of the contact lens. The experimental contact lens 10 also includes supports support multiple components in some supports placed in locations without any components.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments, one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. A contact lens comprising: a body of contact lens material extending between a first surface and a second surface; an electromechanical component supported in the contact lens material between the first surface and the second surface; and a support formed of the contact lens material extending from at least one of the first surface or the second surface to the electromechanical component.

Clause 2. The contact lens of clause 1, wherein the support comprises a plurality of supports each extending from one of the first surface and the second surface to the electromechanical component.

Clause 3. The contact lens of clause 1, wherein the electromechanical component has a first shape and wherein the support is formed with a second shape that corresponds to the first shape.

Clause 4. The contact lens of clause 3, wherein the second shape is the same as the first shape.

Clause 5. The contact lens of clause 1, wherein the support extends from at least one of the first surface and the second surface with a height of at least 0.020 mm.

Clause 6. The contact lens of clause 1, wherein the support extends from at least one of the first surface and the second surface with a height of between 0.020 mm and 0.3 mm.

Clause 7. The contact lens of clause 2, wherein the supports have a width or diameter of at least 0.020 mm.

Clause 8. The contact lens of clause 2, wherein the supports have a width of diameter of between 0.020 mm and 2 mm.

Clause 9. The contact lens of clause 1, wherein a first distance extends between the first surface and the second surface and wherein the support extends from at least of the first surface and the second surface with a height of between 30% and 70% of the first distance.

Clause 10. The contact lens of clause 1, wherein a first distance extends between the first surface and the second surface and wherein the support extends from at least of the first surface and the second surface with a height of less than 50% of the first distance.

Clause 11. The contact lens of clause 1, wherein the support has a volume of between 0.005 uL and 0.5 uL.

Clause 12. The contact lens of clause 1, wherein the support has a volume of between 0.01 uL and 0.1 uL.

Clause 13. The contact lens of clause 1, wherein the electromechanical component includes one or more of a flexible PCB, a power source, a processor, and a light source.

Clause 14. The contact lens of clause 1, wherein the electromechanical component includes a pre-formed flexible PCB having a hemispherical shape.

Clause 15. The contact lens of clause 2, wherein the plurality of supports is arranged in two concentric rings about a clear central zone.

Clause 16. The contact lens of clause 2, wherein the plurality of supports is arranged in a first density to support of first portion of the electromechanical components and in a second density to support a second portion of the electromechanical components.

Clause 17. The contact lens of clause 2, wherein the plurality of supports is arranged with a distance of between 0.10 mm and 1.0 mm from each other.

Clause 18. The contact lens of clause 2, wherein the plurality of supports has a width and are arranged with a distance of between 0.2 widths and 5 widths from each other.

Clause 19. The contact lens of clause 1, wherein the contact lens material comprises a material with a swell of 0% to 2%.

Clause 20. A method of fabricating a contact lens, the method comprising: forming a support of contact lens material on a first contact lens mold; partially curing the support; placing electromechanical components on the support; filling the mold with contact lens material; and curing the contact lens material.

Clause 21. The method of clause 20, wherein forming the support of contact lens material on the first contact lens mold comprises: placing a mask having wells over the first mold; and filling the mask wells with contact lens material.

Clause 22. The method of clause 20, wherein forming the support of contact lens material on the first contact lens mold comprises: coating the first mold with contact lens material, and placing a mask having apertures over the mold; and wherein partially curing the support comprises exposing the contact lens material to curing radiation through the apertures in the mask.

Clause 23. The method of clause 22, wherein forming the support of contact lens material on the first contact lens mold comprises: spin forming the coating on the mold.

Clause 24. The method of clause 20, wherein forming the support of contact lens material on the first contact lens mold comprises: spin forming a coating with a thickness of between 0.001 mm and 0.05 mm on the first mold with contact lens material, and at least partially curing the coating; and forming the support on the at least partially cured coating.

Clause 25. The method of clause 20, further comprising hydrating the cured contact lens material.

Clause 26. The method of clause 20, wherein the support comprises a plurality of supports.

Clause 27. The method of clause 20, wherein the electromechanical component has a first shape and wherein the support is formed with a second shape the corresponds to the first shape.

Clause 28. The method of clause 27, wherein the second shape is the same as the first shape.

Clause 29. The method of any one of clauses 20-24, wherein the support has height of at least 0.020 mm.

Clause 30. The method of any one of clauses 20-24, wherein the support has a height of between 0.020 mm and 0.3 mm.

Clause 31. The method of any one of clauses 20-24, wherein the supports have a width or diameter of at least 0.020 mm.

Clause 32. The method of any one of clauses 20-24, wherein the supports have a width of diameter of between 0.020 mm and 2 mm.

Clause 33. The method of any one of clauses 20-24, wherein the supports have a height of between 30% and 70% of a final thickness of the contact lens.

Clause 34. The method of any one of clauses 20-24, wherein the supports have a height of less than 50% of a final thickness of the contact lens.

Clause 35. The method of any one of clauses 20-24, wherein the support has a volume of between 0.005 uL and 0.5 uL.

Clause 36. The method of any one of clauses 20-24, wherein the support has a volume of between 0.01 uL and 0.1 uL.

Clause 37. The method of any one of clauses 20-24, wherein the electromechanical component includes one or more of a flexible PCB, a power source, a processor, and a light source.

Clause 38. The method of any one of clauses 20-24, wherein the electromechanical component includes a preformed flexible PCB having a hemispherical shape.

Clause 39. The method of any one of clauses 20-24, further comprising: pre-forming a flexible PCB into a hemispherical shape.

Clause 40. The method of any one of clauses 20-24, wherein the plurality of supports is arranged in two concentric rings about a clear central zone.

Clause 41. The method of any one of clauses 20-24, wherein the plurality of supports is arranged in a first density to support of first portion of the electromechanical components and in a second density to support a second portion of the electromechanical components.

Clause 42. The method of any one of clauses 20-24, wherein the plurality of supports is arranged with a distance of between 0.10 mm and 1.0 mm from each other.

Clause 43. The method of any one of clauses 20-24, wherein the plurality of supports has a width and are arranged with a distance of between 0.2 widths and 5 widths from each other.

Clause 44. The method of any one of clauses 20-24, wherein the contact lens material comprises a material with 0% to 2% swell.

Clause 45. The method of any one of clauses 20-24, wherein partially curing the support comprises UV curing, heat curing, or both UV and heat curing.

Clause 46. The method of any one of clauses 20-24, wherein partially curing the contact lens comprises UV curing, heat curing, or both UV and heat curing.

Clause 47. An apparatus for fabricating pillars, the apparatus comprising: a moveable head portion comprising a dispenser and being moveable along a first translational axis; a base comprising a contact lens mold holder and configured to move the contact lens mold about a first and a second axis of rotation; and an arm that couples the head portion to the base.

Clause 48. The apparatus of clause 47, wherein the moveable head portion and the dispense translate along the first translational axis.

Clause 49. The apparatus of clause 47, wherein the first axis of rotation and the second axis of rotation are perpendicular to each other.

Clause 50. The apparatus of clause 47, wherein the first axis of rotation is configured to position the contact lens mold beneath a dispensing conduit of the moveable head portion with a dispensing end of the dispensing conduit offset from a center of the contact lens mold.

Clause 51. The apparatus of clause 50, wherein the second axis of rotation is configured to rotate the contact lens mold while maintaining the offset of the conduit from the center of the contact lens mold.

Clause 52. The apparatus of clause 49, wherein the first axis of rotation is perpendicular to the first translational axis.

Clause 53. The apparatus of clause 47, wherein the contact lens mold holder is rotationally coupled to the base and configured to rotate about the second axis of rotation.

Clause 54. The apparatus of clause 53, wherein the contact lens hold holder includes a plurality of indexes.

Clause 55. The apparatus of clause 54, wherein the indexes are detents.

Clause 56. The apparatus of clause 47, wherein the moveable head portion further comprises a rack and pinion for translating the moveable head portion along the first translation axis.

Clause 57. The contact lens, method or apparatus of any one of the preceding clauses, wherein one or more supports is dimensioned to position a flexible printed circuit board (PCB) with a gap between the flex PCB and a contact lens mold from which the one or more supports extends.

Clause 58. The contact lens, method or apparatus of clause 57, wherein the one or more supports comprises a plurality of supports and wherein the gap between the flex PCB and the contact lens mold extends around each of the plurality of supports.

Clause 59. The contact lens, method or apparatus of clause 57, wherein the gap is dimensioned to receive flowable material for curing to form the contact lens body.

Clause 60. The contact lens, method or apparatus of clause 59, wherein the gap comprises distance extending from flex PCB toward the contact lens mold and is within a range from 0.010 mm to 0.3 mm and optionally within a range from 0.040 mm to 0.2 mm.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A contact lens comprising:
   a body of contact lens material extending between a first surface and a second surface;
   an electromechanical component supported in the contact lens material between the first surface and the second surface; and
   a support formed of the contact lens material extending from at least one of the first surface or the second surface to the electromechanical component, wherein the support comprises a plurality of supports extending from one or more of the first surface or the second surface to the electromechanical component.

2. The contact lens of claim 1, wherein the electromechanical component has a first shape and wherein the support is formed with a second shape that corresponds to the first shape.

3. The contact lens of claim 2, wherein the second shape is the same as the first shape.

4. The contact lens of claim 1, wherein the support extends from at least one of the first surface or the second surface with a height of at least 0.020 mm.

5. The contact lens of claim 1, wherein the support extends from at least one of the first surface or the second surface with a height of between 0.020 mm and 0.3 mm.

6. The contact lens of claim 1, wherein the plurality of supports has a width or diameter of at least 0.020 mm.

7. The contact lens of claim 1, wherein the plurality of supports has a width or diameter of between 0.020 mm and 2 mm.

8. The contact lens of claim 1, wherein a first distance extends between the first surface and the second surface and wherein the support extends from at least one of the first surface or the second surface with a height of between 30% and 70% of the first distance.

9. The contact lens of claim 1, wherein a first distance extends between the first surface and the second surface and wherein the support extends from at least one of the first surface or the second surface with a height of less than 50% of the first distance.

10. The contact lens of claim 1, wherein the support has a volume within a range from 0.005 uL to 0.5 uL.

11. The contact lens of claim 1, wherein the support has a volume within a range from 0.01 uL to 0.1 uL.

12. The contact lens of claim 1, wherein the electromechanical component includes one or more of a flexible PCB, a power source, a processor, and a light source.

13. The contact lens of claim 1, wherein the electromechanical component includes a pre-formed flexible PCB having a hemispherical shape.

14. The contact lens of claim 1, wherein the plurality of supports is arranged in two concentric rings about a clear central zone.

15. The contact lens of claim 1, wherein the plurality of supports is arranged in a first density to support a first portion of the electromechanical components and in a second density to support a second portion of the electromechanical components.

16. The contact lens of claim 1, wherein the plurality of supports is arranged with a distance of between 0.10 mm and 1.0 mm from each other.

17. The contact lens of claim 1, wherein the plurality of supports has a width and are arranged with a distance of between 0.2 widths and 5 widths from each other.

18. The contact lens of claim 1, wherein the contact lens material comprises a material with a swell within a range from 0% to 2%.

19. The contact lens of claim 1, the support is dimensioned to position a flexible printed circuit board (PCB) with a gap between the flex PCB and a contact lens mold from which the one or more plurality of supports extends.

* * * * *